(12) United States Patent
Graham et al.

(10) Patent No.: US 10,865,433 B2
(45) Date of Patent: Dec. 15, 2020

(54) REACTION MIXTURES FOR DIAGNOSING BACTERIAL VAGINOSIS

(71) Applicant: GEN-PROBE INCORPORATED, San Diego, CA (US)

(72) Inventors: Michael Graham, Madison, WI (US); Jeff G. Hall, Waunakee, WI (US); Joseph J. King, Madison, WI (US)

(73) Assignee: GEN-PROBE INCORPORATED, San Diego, CA (US)

( * ) Notice: Subject to any disclaimer, the term of this patent is extended or adjusted under 35 U.S.C. 154(b) by 97 days.

(21) Appl. No.: 15/543,944

(22) PCT Filed: Jan. 8, 2016

(86) PCT No.: PCT/US2016/012589
§ 371 (c)(1),
(2) Date: Jul. 14, 2017

(87) PCT Pub. No.: WO2016/112252
PCT Pub. Date: Jul. 14, 2016

(65) Prior Publication Data
US 2018/0171375 A1 Jun. 21, 2018

Related U.S. Application Data

(60) Provisional application No. 62/101,907, filed on Jan. 9, 2015.

(51) Int. Cl.
*C12Q 1/689* (2018.01)
*C12Q 1/04* (2006.01)
(Continued)

(52) U.S. Cl.
CPC ............... *C12Q 1/04* (2013.01); *C12Q 1/689* (2013.01); *C12Q 1/6883* (2013.01);
(Continued)

(58) Field of Classification Search
CPC ...................................................... C12Q 1/689
See application file for complete search history.

(56) References Cited

U.S. PATENT DOCUMENTS

| | | |
|---|---|---|
| 2003/0152942 A1 | 8/2003 | Fors et al. |
| 2011/0151462 A1 | 6/2011 | Tynan et al. |
| 2011/0212852 A1 | 9/2011 | Getman |

FOREIGN PATENT DOCUMENTS

| | | | | |
|---|---|---|---|---|
| WO | WO-9947706 A1 * | 9/1999 | ........... | C12Q 1/6874 |
| WO | 2011068679 A1 | 6/2011 | | |

OTHER PUBLICATIONS

EPO Extended European Search Report, European Application No. 16735450.5, dated Aug. 23, 2018.
(Continued)

*Primary Examiner* — Diana B Johannsen
(74) *Attorney, Agent, or Firm* — Nicholas V. Sherbina; Jeffrey E. Landes

(57) ABSTRACT

Disclosed are methods for diagnosing Bacterial Vaginosis (BV). The disclosed methods generally include detecting select species of *Eggerthella* and/or *Prevotella*, and optionally detecting select species of *Lactobacillus*. Also disclosed are nucleic acid oligomers and related compositions for detection of a 16S rRNA or its encoding gene from select species of *Eggerthella*, *Prevotella*, or *Lactobacillus*.

9 Claims, 13 Drawing Sheets

Specification includes a Sequence Listing.

(51) Int. Cl.
*G01N 33/68* (2006.01)
*C12Q 1/6883* (2018.01)
*G01N 33/533* (2006.01)

(52) U.S. Cl.
CPC ....... *G01N 33/533* (2013.01); *G01N 33/6893* (2013.01); *G01N 2800/26* (2013.01); *G01N 2800/36* (2013.01)

(56) References Cited

OTHER PUBLICATIONS

Datcu et al., "Bacterial Vaginosis Diagnosed by Analysis of First-Void-Urine Specimens," Journal of Clinical Microbiology, 2014, vol. 52, No. 1, p. 218-225.
Fredricks et al., "Molecualr Identification of Bacteria Associated with Bacterial Vaginosis," The New England Journal of Medicine, 2005, p. 1899-1911, XP055499719.
Twin et al., "The Potential of Metatranscriptomics for Ideifying Screening Targets for Bacterial Vaginosis," PLOS ONE, 2013, vol. 8, No. 9, p. 1-17, XP055488517.
PCT International Preliminary Report on Patentability, International Application No. PCT/US2016/012589, dated Jul. 11, 2017.
PCT Written Opinion, International Application No. PCT/US2016/012589, dated May 20, 2016.
PCT International Search Report, International Application No. PCT/US2016/012589, dated May 20, 2016.
Fredricks et al., "Targeted PCR for Detection of Vaginal Bacteria Associated with Bacterial Vaginosis," Journal of Clinical Microbiology, 2007, vol. 45, No. 10, p. 3270-3276.
Liu et al., "Comparative Analysis of Vaginal Bacterial Diversity in Northern-Chinese Women Associated With or Without Bacterial Vaginosis," Journal of Medical Microbiology and Diagnosis, 2012, vol. S5, p. 1-9.
Shipitsyna et al., "Composition of the Vaginal Microbiota in Women of Reproductive Age—Sensitive and Specific Molecular Diagnosis of Bacterial Vaginosis is Possible?," 2013, vol. 8, Issue 4, p. 1-10.

* cited by examiner

```
CGCCCTTAGAGTTTGATCCTGGCTCAGGATGAACGCTGGCGGCGTGCCTAACACATGCAA
GTCGAACGATTAAAGCACCTTCGGGTGTGTATAGAGTGGCGAACGGGTGAGTAACACGTG
ACCAACCTGCCTCTTACATTGGGACAACCAAAAGAAATTCTGGCTAATACCAAATACTCC
GCACATATCACATGATGTATGCGGGAAAGCTTTTGCGGTAAGAGATGGGGTCGCGGCCCA
TTAGGTAGACGGCGGGGTAGAAGCCCACCGTGCCGATGATGGGTAGCCGGGTTGAGAGAC
CGACCGGCCACATTGGGACTGAGATACGGCCCAGACTCCTACGGGAGGCAGCAGTGGGGA
ATATTGCGCAATGGGGGAAACCCTGACGCAGCAACGCCGCGTGCGGGATGAAGGCCTTCG
GGTTGTAAACCGCTTTCAGCAGGGAAGACATCGACGGTACCTGCAGAAGAAGCCCCGGCT
AACTACGTGCCAGCAGCCGCGGTAATACGTAGGGGGCGAGCGTTATCCGGATTCATTGGG
CGTAAAGCGCGCGCAGGCGGTTGCTCAAGCGGAACCTCTAATCTCGGGGCTTAACCTCGA
GCCGGGTTCCGAACTGGACGACTCGAGTGCGGTAGAGGCAGATGGAATTCCCGGTGTAGC
GGTGGAATGCGCAGATATCGGGAAGAACACCAACGGCGAAGGCAGTCTGCTGGGCCGTCA
CTGACGCTGAGGCGCGAAAGCTGGGGGAGCGAACAGGATTAGATACCCTGGTAGTCCCAG
CCGTAAACGATGAGCGCTGGGTGTGGGAGATTACATCTTCCGTGCCGAAGCTAACGCATT
AAGCGCTCCGCCTGGGGAGTACGGCCGCAAGGCTAAAACTCAAAGGAATTGACGGGGGCC
CGCACAAGCAGCGGAGCATGTGGCTTAATTCGAAGCAACGCGAAGAACCTTACCAGGGCT
TGACATGTAGGTGAAGCGGCGGAAACGTCGTGGCCGAAAGGAGCCTACACAGGTGGTGCA
TGGCTGTCGTCAGCTCGTGTCGTGAGATGTTGGGTTAAGTCCCGCAACGAGCGCAACCCC
TGCCCCGTGTTACCAGCATTTAGTTGGGGACTCGCGGGGACTGCCGGCGTCAAGCCGGA
GGAAGGCGGGGATGACGTCAAGTCATCATGCCCCTTATGCCCTGGGCCGCACACGTGCTA
CAATGGCCGGCACAGCGGGCTGCAACCTAGCGATAGGAAGCGAATCCCGTAAAGCCGGTC
CCAGTTCGGATTGGAGGCTGAAACCCGCCTCCATGAAGCCGGAGTTGCTAGTAATCGCGG
ATCAGCACGCCGCGGTGAATGCGTTCCCGGGCCTTGTACACACCGCCCGTCACACCACCC
GAGTCGTCTGCACCCGAAGCCGCCGGCCGAACCCCTTTGGGGACGGAGGCGTCGAAGGTG
TGGAGGGTGAGGGGGGTGAAGTCGTAACAAGGTAACCGTAAAGGGC
```

FIG. 1

```
TGTGTAGCGGTGAAATGYGTAGATATARGAAGGAACATCAGTGGCGAAGGCGACCACCKG
GWCWGATASTGACASTGAGGTGCGAAAGCGTGGGGAGCRAACAGGATTAGATACCSTGGT
AGTCCACGCCGTAAACGATGTCAACTTGGCTCAGGATGAACGCTAGCTATAGGCTTAACA
CATGCAAGTCGAGGGGCAGCGAATAGATAGCTTGCTATTTATGTCGGCGACCGGCGCACG
GGTGAGTAACGCGTATCCAACCTGCCCATAACTAAGGGATAACCCAGCGAAAGTTGGACT
AATACCTTATGTATTCGTTTGATCTCATGAGATTAYGAATAAAGATTTATCGGTTATGGA
TGGGGATGCGTCTGATTAGCTTGTTGGCGGGGTAACGGCCCACCAAGGCAACGATCAGTA
GGGGTTCTGAGAGGAAGGTCCCCCACATTGGAACTGAGACACGGTCCAAACTCCTACGGG
AGGCAGCAGTGAGGAATATTGGTCAATGGACGCAAGTCTGAACCAGCCAAGTAGCGTGCA
GGATGACGGCYCTATGGGTTGTAAACTGCTTTTATATGGGGATAAAGTGGGGAACGTGTT
CCCTTTTGCAGGTACCATATGAATAAGGACCGGCTAATTCCGTGCCAGCAGCCGCGGTAA
TACGGAAGGTTCGGGCGTTATCCGGATTTATTGGGTTTAAAGGGAGCGTAGGCCGTTTGG
TAAGCGTGTTGTGAAATGTAGGAGCTCAACTTCTAGATTGCAGCGCGAACTGTCAGACTT
GAGTGCGCACAACGTAGGCGGAATTCATGGTGTAGCGGTGAAATGCTTAGATATCATGAA
GAACTCCGATTGCGAAGGCAGCTTACGGGARCGCAACTGACGCTGAAGCTCGAAGGTGCG
GGTATCGAACAGGATTAGATACCCTGGTAGTCCGCACAGTAAACGATGGATGCCCGCTGT
TAGCACCTAGTGTTAGCGGCTAAGCGAAAGCATTAAGCATCCCACCTGGGGAGTACGCCG
GCAACGGTGAAACTCAAAGGAATTGACGGGGGCCCGCACAAGCGGAGGAACATGTGGTTT
AATTCGATGATACGCGAGGAACCTTACCCGGGCTTGAATTGCAGATGAACGATTTAGAGA
TAATGAGGTCCTTCGGGACATCTGTGAAGGTGCTGCATGGTTGTCGTCAGCTCGTGCCGT
GAGGTGTCGGCTTAAGTGCCATAACGAGCGCAACCCCTTTCTTTAGTTGCCATCAGGTYM
TGCTGGGCACTCTGGAGATACTGCCACCGTAAGGTGTGAGGAAGGTGGGGATGACGTCAA
ATCAGCACGGYCCTTACGTCCGGGCTACACACGTGTTACAATGGGTGGTACAGATAGTT
GGTCGTRTGCAAATACGATCTAATCCTTAAAACCATTCTCAGTTCGGACTGGGGTCTGCA
ACCCGACCCCACGAAGCTGGATTCGCTAGTAATCGCGCATCAGCCATGGCGCGGTGAATA
CGTTCCCGGGCCTTGTACACACCGCCCGTCAAGCCATGAAAGCCGGGGTGCC
```

FIG. 2

```
TTAATAAAGTCGCTTCGAGAGATGCGACGAGAGCTTAAAAACAGACATGTAAGGAAAGAA
AACAAATAAAAAGAAAAAAGTACTTGCAAAGAAGTAAATAAGCTGGTAATATATTTAAAT
GTCGTCAGGCGAAAGCAGAAAAAGCTTGAGCAAGACGAAAAAAACAAATCAAAAAAGTTC
TTGACAAAGAAATGATGGTTTGATAAAATATAAAAGCTGTCTGCTTTACAAAAAGCAAGA
CAGAGGTAGTACTTTGAAAACTGAACAAAGTTTCGCTAAAAGTGTGCGGGTGTAAAAACC
CAAACAAGAAGCGAAGTCAATTCGCAAGCAATAAATTTGAGACAAAGATCTTAAATAAGG
AATGAGCAATCATTCAAACTTTTTAAAATGAGAGTTTGATCCTGGCTCAGGACGAACGCT
GGCGGCGTGCCTAATACATGCAAGTCGAGCGAGCGGAACTAACAGATTTACTTCGGTAAT
GACGTTAGGAAAGCGAGCGGCGGATGGGTGAGTAACACGTGGGGAACCTGCCCCATAGTC
TGGGATACCACTTGGAAACAGGTGCTAATACCGGATAAGAAAGCAGATCGCATGATCAGC
TTTTAAAAGGCGGCGTAAGCTGTCGCTATGGGATGGCCCCGCGGTGCATTAGCTAGTTGG
TAAGGTAAAGGCTTACCAAGGCGATGATGCATAGCCGAGTTGAGAGACTGATCGGCCACA
TTGGGACTGAGACACGGCCCAAACTCCTACGGGAGGCAGCAGTAGGGAATCTTCCACAAT
GGACGCAAGTCTGATGGAGCAACGCCGCGTGAGTGAAGAAGGTTTTCGGATCGTAAAGCT
CTGTTGTTGGTGAAGAAGGATAGAGGTAGTAACTGGCCTTTATTTGACGGTAATCAACCA
GAAAGTCACGGCTAACTACGTGCCAGCAGCCGCGGTAATACGTAGGTGGCAAGCGTTGTC
CGGATTTATTGGGCGTAAAGCGAGCGCAGGCGGAAGAATAAGTCTGATGTGAAAGCCCTC
GGCTTAACCGAGGAACTGCATCGGAAACTGTTTTTCTTGAGTGCAGAAGAGGAGAGTGGA
ACTCCATGTGTAGCGGTGGAATGCGTAGATATATGGAAGAACACCAGTGGCGAAGGCGGC
TCTCTGGTCTGCAACTGACGCTGAGGCTCGAAAGCATGGGTAGCGAACAGGATTAGATAC
CCTGGTAGTCCATGCCGTAAACGATGAGTGCTAAGTGTTGGGAGGTTTCCGCCTCTCAGT
GCTGCAGCTAACGCATTAAGCACTCCGCCTGGGGAGTACGACCGCAAGGTTGAAACTCAA
AGGAATTGACGGGGGCCCGCACAAGCGGTGGAGCATGTGGTTTAATTCGAAGCAACGCGA
AGAACCTTACCAGGTCTTGACATCTAGTGCCATTTGTAGAGATACAAAGTTCCCTTCGGG
GACGCTAAGACAGGTGGTGCATGGCTGTCGTCAGCTCGTGTCGTGAGATGTTGGGTTAAG
TCCCGCAACGAGCGCAACCCTTGTTATTAGTTGCCAGCATTAAGTTGGGCACTCTAATGA
GACTGCCGGTGACAAACCGGAGGAAGGTGGGGATGACGTCAAGTCATCATGCCCCTTATG
ACCTGGGCTACACACGTGCTACAATGGGCAGTACAACGAGAAGCGAGCCTGCGAAGGCAA
GCGAATCTCTGAAAGCTGTTCTCAGTTCGGACTGCAGTCTGCAACTCGACTGCACGAAGC
TGGAATCGCTAGTAATCGCGGATCAGCACGCCGCGGTGAATACGTTCCCGGGCCTTGTAC
ACACCGCCCGTCACACCATGGGAGTCTGCAATGCCCAAAGCCGGTGGCCTAACCTTCGGG
AAGGAGCCGTCTAAGGCAGGGCAGATGACTGGGGTGAAGTCGTAACAAGGTAGCCGTAGG
AGAACCTGCGGCTGGATCACCTCCTTTCTAAGGAAGCGAAGGATATGGAGAGCAGGAATG
CTAAGAGAAGTATCCAGAGCAAGCGGAAGCACACTGAGAAACTTTGTTTAGTTTTGAGGG
TAGTACCTC
```

FIG. 3

SEQUENCE LISTING

<160> NUMBER OF SEQ ID NOS: 16

<210> SEQ ID NO 1
<211> LENGTH: 1486
<212> TYPE: DNA
<213> ORGANISM: Eggerthella
<300> PUBLICATION INFORMATION:
<308> DATABASE ACCESSION NUMBER: GenBank / AY959023.1
<309> DATABASE ENTRY DATE: 2008-04-17
<313> RELEVANT RESIDUES IN SEQ ID NO: (1)..(1486)

<400> SEQUENCE: 1

| | | | | | | |
|---|---|---|---|---|---|---|
| cgcccttaga | gtttgatcct | ggctcaggat | gaacgctggc | ggcgtgccta | acacatgcaa | 60 |
| gtcgaacgat | taaagcacct | tcgggtgtgt | atagagtggc | gaacgggtga | gtaacacgtg | 120 |
| accaacctgc | ctcttacatt | gggacaacca | aaagaaattc | tggctaatac | caaatactcc | 180 |
| gcacatatca | catgatgtat | gcgggaaagc | ttttgcggta | agagatgggg | tcgcggccca | 240 |
| ttaggtagac | ggcggggtag | aagcccaccg | tgccgatgat | gggtagccgg | gttgagagac | 300 |
| cgaccggcca | cattgggact | gagatacggc | ccagactcct | acgggaggca | gcagtgggga | 360 |
| atattgcgca | atgggggaaa | ccctgacgca | gcaacgccgc | gtgcgggatg | aaggccttcg | 420 |
| ggttgtaaac | cgctttcagc | agggaagaca | tcgacggtac | ctgcagaaga | agccccggct | 480 |
| aactacgtgc | cagcagccgc | ggtaatacgt | aggggggcgag | cgttatccgg | attcattggg | 540 |
| cgtaaagcgc | gcgcaggcgg | ttgctcaagc | ggaacctcta | atctcggggc | ttaacctcga | 600 |
| gccgggttcc | gaactggacg | actcgagtgc | ggtagaggca | gatggaattc | ccggtgtagc | 660 |
| ggtggaatgc | gcagatatcg | ggaagaacac | caacggcgaa | ggcagtctgc | tgggccgtca | 720 |
| ctgacgctga | ggcgcgaaag | ctgggggagc | gaacaggatt | agataccctg | gtagtcccag | 780 |
| ccgtaaacga | tgagcgctgg | gtgtgggaga | ttacatcttc | cgtgccgaag | ctaacgcatt | 840 |
| aagcgctccg | cctggggagt | acggccgcaa | ggctaaaact | caaaggaatt | gacggggggcc | 900 |
| cgcacaagca | gcggagcatg | tggcttaatt | cgaagcaacg | cgaagaacct | taccagggct | 960 |
| tgacatgtag | gtgaagcggc | ggaaacgtcg | tggccgaaag | gagcctacac | aggtggtgca | 1020 |
| tggctgtcgt | cagctcgtgt | cgtgagatgt | tgggttaagt | cccgcaacga | gcgcaacccc | 1080 |
| tgccccgtgt | taccagcatt | tagttgggga | ctcgcggggg | actgccggcg | tcaagccgga | 1140 |
| ggaaggcggg | gatgacgtca | agtcatcatg | ccccttatgc | cctgggccgc | acacgtgcta | 1200 |
| caatggccgg | cacagcgggc | tgcaacctag | cgataggaag | cgaatcccgt | aaagccggtc | 1260 |
| ccagttcgga | ttggaggctg | aaacccgcct | ccatgaagcc | ggagttgcta | gtaatcgcgg | 1320 |
| atcagcacgc | cgcggtgaat | gcgttccgg | gccttgtaca | caccgcccgt | cacaccaccc | 1380 |
| gagtcgtctg | cacccgaagc | cgccggccga | acccctttgg | ggacggaggc | gtcgaaggtg | 1440 |
| tggagggtga | gggggggtgaa | gtcgtaacaa | ggtaaccgta | aagggc | | 1486 |

<210> SEQ ID NO 2
<211> LENGTH: 1553
<212> TYPE: DNA
<213> ORGANISM: Prevotella bivia
<300> PUBLICATION INFORMATION:
<308> DATABASE ACCESSION NUMBER: GenBank / JN867270.1
<309> DATABASE ENTRY DATE: 2012-03-30
<313> RELEVANT RESIDUES IN SEQ ID NO: (1)..(1553)

<400> SEQUENCE: 2

| | | | | | | |
|---|---|---|---|---|---|---|
| tgtgtagcgg | tgaaatgygt | agatatarga | aggaacatca | gtggcgaagg | cgaccacckg | 60 |
| gwcwgatast | gacastgagg | tgcgaaagcg | tggggagcra | acaggattag | ataccstggt | 120 |

```
agtccacgcc gtaaacgatg tcaacttggc tcaggatgaa cgctagctat aggcttaaca      180
catgcaagtc gaggggcagc gaatagatag cttgctattt atgtcggcga ccggcgcacg      240
ggtgagtaac gcgtatccaa cctgcccata actaagggat aacccagcga agttggact       300 aataccttat gtattcgttt gatctcatga gattaygaat aaagatttat cggttatgga      360
tggggatgcg tctgattagc ttgttggcgg ggtaacggcc caccaaggca acgatcagta      420
ggggttctga gaggaaggtc ccccacattg gaactgagac acggtccaaa ctcctacggg      480
aggcagcagt gaggaatatt ggtcaatgga cgcaagtctg aaccagccaa gtagcgtgca      540
ggatgacggy ctatgggtt gtaaactgct tttatatggg gataaagtgg ggaacgtgtt      600 ccctttgca ggtaccatat gaataaggac cggctaattc cgtgccagca gccgcggtaa       660 tacgaaggt cgggcgtta ccggattta ttgggtttaa agggagcgta ggccgtttgg         720
taagcgtgtt gtgaaatgta ggagctcaac ttctagattg cagcgcgaac tgtcagactt      780
gagtgcgcac aacgtaggcg gaattcatgg tgtagcggtg aaatgcttag atatcatgaa      840
gaactccgat tgcgaaggca gcttacggga rcgcaactga cgctgaagct cgaaggtgcg      900
ggtatcgaac aggattagat accctggtag tccgcacagt aaacgatgga tgcccgctgt      960
tagcacctag tgttagcggc taagcgaaag cattaagcat cccacctggg gagtacgccg     1020
gcaacggtga aactcaaagg aattgacggg ggcccgcaca gcggaggaa catgtggttt      1080 aattcgatga tacgcgagga accttacccg ggcttgaatt gcagatgaac gatttagaga     1140
taatgaggtc cttcgggaca tctgtgaagg tgctgcatgg ttgtcgtcag ctcgtgccgt     1200
gaggtgtcgg cttaagtgcc ataacgagcg caacccccttt ctttagttgc catcaggtym    1260
tgctgggcac tctggagata ctgccaccgt aaggtgtgag gaaggtgggg atgacgtcaa     1320
atcagcacgg yccttacgtc cggggctaca cacgtgttac aatgggtggt acagatagtt     1380
ggtcgtrtgc aaatacgatc taatccttaa aaccattctc agttcggact ggggtctgca     1440
acccgacccc acgaagctgg attcgctagt aatcgcgcat cagccatggc gcggtgaata     1500
cgttcccggg ccttgtacac accgcccgtc aagccatgaa agccgggggt gcc            1553
```

<210> SEQ ID NO 3
<211> LENGTH: 2049
<212> TYPE: DNA
<213> ORGANISM: Lactobacillus crispatus
<300> PUBLICATION INFORMATION:
<308> DATABASE ACCESSION NUMBER: GenBank / FN692037.1
<309> DATABASE ENTRY DATE: 2010-06-24
<313> RELEVANT RESIDUES IN SEQ ID NO: (1)..(2049)

<400> SEQUENCE: 3

```
ttaataaagt cgcttcgaga gatgcgacga gagcttaaaa acagacatgt aaggaaagaa       60
aacaaataaa aagaaaaaag tacttgcaaa gaagtaaata agctggtaat atatttaaat     120
gtcgtcaggc gaaagcagaa aaagcttgag caagacgaaa aaaacaaatc aaaaaagttc     180
ttgacaaaga aatgatggtt tgataaaata taaaagctgt ctgctttaca aaaagcaaga     240
cagaggtagt actttgaaaa ctgaacaaag tttcgctaaa agtgtgcggg tgtaaaaacc     300
caaacaagaa gcgaagtcaa ttcgcaagca ataaatttga dacaaagatc ttaataagg    360 aatgagcaat cattcaaact tttaaaatg agagtttgat cctggctcag gacgaacgct      420
ggcggcgtgc ctaatacatg caagtcgagc gagcggaact aacagattta cttcggtaat     480
gacgttagga aagcgagcgg cggatgggtg agtaacacgt ggggaacctg ccccatagtc     540
```

```
tgggatacca cttggaaaca ggtgctaata ccggataaga aagcagatcg catgatcagc    600
ttttaaaagg cggcgtaagc tgtcgctatg ggatggcccc gcggtgcatt agctagttgg    660
taaggtaaag gcttaccaag gcgatgatgc atagccgagt tgagagactg atcggccaca    720
ttgggactga gacacggccc aaactcctac gggaggcagc agtagggaat cttccacaat    780
ggacgcaagt ctgatggagc aacgccgcgt gagtgaagaa ggttttcgga tcgtaaagct    840
ctgttgttgg tgaagaagga tagaggtagt aactggcctt tatttgacgg taatcaacca    900
gaaagtcacg gctaactacg tgccagcagc cgcggtaata cgtaggtggc aagcgttgtc    960
cggatttatt gggcgtaaag cgagcgcagg cggaagaata agtctgatgt gaaagccctc   1020
ggcttaaccg aggaactgca tcggaaactg ttttcttga gtgcagaaga ggagagtgga   1080
actccatgtg tagcggtgga atgcgtagat atatggaaga acaccagtgg cgaaggcggc   1140
tctctggtct gcaactgacg ctgaggctcg aaagcatggg tagcgaacag gattagatac   1200
cctggtagtc catgccgtaa acgatgagtg ctaagtgttg ggaggtttcc gcctctcagt   1260
gctgcagcta acgcattaag cactccgcct ggggagtacg accgcaaggt tgaaactcaa   1320
aggaattgac gggggcccgc acaagcggtg gagcatgtgg tttaattcga agcaacgcga   1380
agaaccttac caggtcttga catctagtgc catttgtaga gatacaaagt tcccttcggg   1440
gacgctaaga caggtggtgc atggctgtcg tcagctcgtg tcgtgagatg ttgggttaag   1500
tcccgcaacg agcgcaaccc ttgttattag ttgccagcat taagttgggc actctaatga   1560
gactgccggt gacaaaccgg aggaaggtgg ggatgacgtc aagtcatcat gccccttatg   1620
acctgggcta cacacgtgct acaatgggca gtacaacgag aagcgagcct gcgaaggcaa   1680
gcgaatctct gaaagctgtt ctcagttcgg actgcagtct gcaactcgac tgcacgaagc   1740
tggaatcgct agtaatcgcg gatcagcacg ccgcggtgaa tacgttcccg ggccttgtac   1800
acaccgcccg tcacaccatg ggagtctgca atgcccaaag ccggtggcct aaccttcggg   1860
aaggagccgt ctaaggcagg gcagatgact ggggtgaagt cgtaacaagg tagccgtagg   1920
agaacctgcg gctggatcac ctcctttcta aggaagcgaa ggatatggag agcaggaatg   1980
ctaagagaag tatccagagc aagcggaagc acactgagaa actttgttta gttttgaggg   2040
tagtacctc                                                          2049
```

<210> SEQ ID NO 4
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 4

```
gactaacaac gaggcagatg gaattcc                                        27
```

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5

```
tggacgactc gagtgcggta a                                              21
```

<210> SEQ ID NO 6
<211> LENGTH: 18

<212> TYPE: DNA
<213> ORGANISM: Artificial Sequence
<220> FEATURE:
<223> OTHER INFORMATION: Synthetic Oligonucleotide

<400> SEQUENCE: 6
gatatctgcg cattccac                                                 18

<210> SEQ ID NO 7
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 7
gacccttatt ggctaagcga aagca                                         25

<210> SEQ ID NO 8
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 8
ccgctgttag cacctagtgt tagca                                         25

<210> SEQ ID NO 9
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 9
ttgagtttca ccgttgc                                                  17

<210> SEQ ID NO 10
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 10
acagcaaata aggtagtaac tggcctt                                       27

<210> SEQ ID NO 11
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 11
agctctgttg ttggtgaaga aggatagc                                      28

<210> SEQ ID NO 12
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 12

```
cgtaaagctc tgttggtagt gaagaaagat agc                              33

<210> SEQ ID NO 13
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 13
tacgtattac cgcggct                                                17

<210> SEQ ID NO 14
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 14
tcttagccgg ttttccggct gagagttgtt agtc                             34

<210> SEQ ID NO 15
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 15
tcttagccgg ttttccggct gagaaataag ggtc                             34

<210> SEQ ID NO 16
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 16
tcttagccgg ttttccggct gagatatttg ctgt                             34
```

REACTION MIXTURES FOR DIAGNOSING BACTERIAL VAGINOSIS

CROSS-REFERENCE TO RELATED APPLICATIONS

This application is a national stage entry of International Patent Application No. PCT/US2016/012589, filed Jan. 8, 2016, and claims priority under 35 U.S.C. .sctn.119(e) to U.S. Provisional App. No. 62/101,907 filed on Jan. 9, 2015, the entire contents of both are incorporated herein by reference.

BACKGROUND

According to the National Health and Nutrition Examination Survey, nearly a third of women between the age of 14 and 49 have bacterial vaginosis (BV). See Allsworth and Peipert, *Obstetrics and Gynecology* 109:114-120, 2007). BV is the most common cause of vaginal discharge and a reason many women seek medical attention. It is also associated with preterm birth, low birth weight, pelvic inflammatory disease, an increase in STD infections, including HIV, and a greater risk of passing HIV on to sex partners. See Srinivasan and Fredricks, *Interdisciplinary Perspectives on Infectious Diseases*, Vol. 2008, Article ID 750479, 22 pages, 2008). Women with bacterial vaginosis may have symptoms including a malodorous vaginal discharge or irritation, however, as many as half of the women with diagnosable BV have no clear symptoms (see Srivinvasan and Fredricks, supra).

Most researchers and the CDC consider bacterial vaginosis to be the result of a disruption to the normal bacterial flora of the vagina. Unlike common infections, this dysbiosis is not the result of an individual bacterial species. See CDC Factsheet, 2014 (BV-Fact-Sheet-March-2014.pdf, from CDC website). A dysbiosis is a disruption of the normal microbiota within a body environment such as the vagina. See Nibali et al., *Journal of Oral Microbiology* 6:22962, 2014.

BV is diagnosed in the clinic using the Amsel Criteria and in the laboratory using the Nugent Scoring System. The later relies on counting bacterial morphotypes with the aid of the Gram stain. In this way, the Nugent Score is a visual assessment of dysbiosis—it scores the bad bacteria against the good. See Nugent et al., *Journal of Clinical Microbiology* 29:297-301, 1991. The Amsel Criteria evaluates a sample for the presence of clue cells, pH, color and odor which are key symptoms associated with BV. See Amsel et al., *Am. J. Med.* 74:14-22, 1983. A wet mount of the sample is examined with a microscope to detect clue cells which are human epithelial cells covered with bacteria thought to predominately consist of *G. vaginalis*.

Molecular tests generally target multiple organisms which have strong correlations with bacterial vaginosis. Which organisms are targeted varies from test to test. In nearly all cases, high abundance anaerobic bacteria are targeted such as *Atopobium*, *Gardnerella*, and *Megasphaera* species.

The only FDA approved test for BV (BD Affirm VPIII 2010), was found to have a sensitivity of 67.6% and a specificity of 76.4% in a study by Cartwright et al. (*Journal of Clinical Microbiology* 51:3694-3699, 2013). For the purpose diagnosing BV, the Affirm product detects *G. vaginalis* as its sole indicator. The product package insert indicates the Affirm product is 95.1% sensitive and 83.3% specific when compared to a scored gram stain method.

Cartwright et al., supra, used a multiplex assay for the detection of *Atopobium vaginae*, BVAB-2 and *Megasphaera*-1 for the diagnosis of BV. They measured the performance of this assay against a combination of Nugent and Amsel results in a population of 323 women (93% African-American, 7% white non-Hispanic). They reported this test was 96.9% sensitive and 92.6% specific when compared to the combination of Nugent and Amsel scores. They did not report the results of this assay relative to the Nugent Score alone.

SUMMARY

In one aspect, the present invention provides a method for diagnosing Bacterial Vaginosis (BV) in a subject. The method generally includes (a) providing a sample from a subject suspected of having BV; and (b) performing an assay for the detection of select bacterial species in each of the genera *Eggerthella* and *Prevotella* in the sample, where the assay detects an *Eggerthella* species characterized by the presence of a 16S rRNA gene having a nucleobase sequence that is at least 98% identical (e.g., at least 99% or 100% identical) to the sequence shown in SEQ ID NO:1 but does not detect other *Eggerthella* species, where the assay detects *P. amnii*, *P. disiens*, and *P. bivia* but does not detect other *Prevotella* species. The detection of at least one of *Eggerthella* and *Prevotella* indicates BV in the subject.

In certain embodiments of a method as above, the assay for detection of *Eggerthella* and *Prevotella* is a nucleic-acid-based detection assay. In some such embodiments, the nucleic-acid-based detection assay targets the 16S rRNA of *Eggerthella* and *Prevotella*. In particular variations, the nucleic-acid-based detection assay targets (i) an *Eggerthella* 16S rRNA region corresponding to nucleotide positions 615 to 679 of SEQ ID NO:1, and/or (ii) a *Prevotella* 16S rRNA region corresponding to nucleotide positions 954 to 1037 of SEQ ID NO:2. In other embodiments, the nucleic-acid-based detection assay is a non-amplification-based assay such as, for example, a cleavage-based assay. In some such embodiments, the cleavage-based assay detects an RNA target nucleic acid and utilizes a flap endonuclease that is capable of cleaving an RNA:DNA linear duplex structure; in other embodiments, the cleavage-based assay detects a DNA target nucleic acid and utilizes a flap endonuclease that is capable of cleaving a DNA:DNA linear duplex structure. In some variations of a method employing a nucleic-acid-based detection assay, the detection of *Eggerthella* and *Prevotella* is performed using a homogeneous detection reaction. The detection of *Eggerthella* and *Prevotella* may further be performed in real time.

In some embodiments of a method utilizing a cleavage-based assay, the assay includes the following steps:
  (i) contacting the sample with (A) an *Eggerthella*-specific primer that specifically hybridizes to a target sequence within SEQ ID NO:1, and (B) a *Prevotella*-specific primer that specifically hybridizes to a target sequence within SEQ ID NO:2, where the contacting is performed under reaction conditions whereby each primer specifically hybridizes to its respective 16S rRNA target sequence within an *Eggerthella* target 16S rRNA or a *Prevotella* target 16S rRNA, if present;
  (ii) providing reactions conditions whereby the 3' end of each hybridized primer is extended, thereby generating a single-stranded cDNA having a sequence complementary to a region of the *Eggerthella* or *Prevotella* target 16S rRNA, the region located 5' to the respective primer target sequence;

(iii) contacting any *Eggerthella* or *Prevotella* cDNA from step (ii) with (A) a first *Eggerthella* probe oligonucleotide having a 3' portion that specifically hybridizes to a first target sequence within the *Eggerthella* cDNA and a 5' portion that does not specifically hybridize to the *Eggerthella* cDNA, (B) a first *Prevotella* probe oligonucleotide having a 3' portion that specifically hybridizes to a first target sequence within the *Prevotella* cDNA and a 5' portion that does not specifically hybridize to the *Prevotella* cDNA, (C) a second *Eggerthella* probe oligonucleotide having a 5' portion that specifically hybridizes to a second target sequence with the *Eggerthella* cDNA, where the second *Eggerthella* cDNA target sequence is located 3' and adjacent to the first *Eggerthella* cDNA target sequence, and (D) a second *Prevotella* probe oligonucleotide having a 5' portion that specifically hybridizes to a second target sequence with the *Prevotella* cDNA, where the second *Prevotella* cDNA target sequence is located 3' and adjacent to the first *Prevotella* cDNA target sequence, where the contacting is performed under reaction conditions whereby if the *Eggerthella* cDNA is present, the first and second *Eggerthella* probe oligonucleotides stably hybridize to the *Eggerthella* cDNA so as to form an *Eggerthella* linear duplex cleavage structure, and if the *Prevotella* cDNA is present, the first and second *Prevotella* probe oligonucleotides stably hybridize to the *Prevotella* cDNA so as to form a *Prevotella* linear duplex cleavage structure;

(iv) contacting the sample with a flap endonuclease capable of cleaving any cleavage structure from step (iii) under reaction conditions whereby if the *Eggerthella* cleavage structure is present, cleavage of the *Eggerthella* cleavage structure occurs to generate a *Eggerthella* cleavage product comprising the 5' portion of the first *Eggerthella* probe oligonucleotide, and if the *Prevotella* cleavage structure is present, cleavage of the *Prevotella* cleavage structure occurs to generate a *Prevotella* cleavage product comprising the 5' portion of the first *Prevotella* probe oligonucleotide; and (v) detecting the presence or absence of the *Eggerthella* and *Prevotella* cleavage products.

In some variations of a method comprising a cleavage-based assay as above, any one or more of the following conditions is present: the *Eggerthella*-specific primer comprises the sequence shown in SEQ ID NO:6; the *Prevotella*-specific primer comprises the sequence shown in SEQ ID NO:9; the 3' portion of the first *Eggerthella* probe oligonucleotide comprises the sequence shown in residues 11-27 of SEQ ID NO:4; the 3' portion of the first *Prevotella* probe oligonucleotide comprises the sequence shown in residues 11-25 of SEQ ID NO:7; the 5' portion of the second *Eggerthella* probe oligonucleotide comprises the sequence shown in residues 1-20 of SEQ ID NO:5; and/or the 5' portion of the second *Prevotella* probe oligonucleotide comprises the sequence shown in residues 1-24 of SEQ ID NO:8.

In certain embodiments of a method comprising a cleavage-based assay as above, detecting the *Eggerthella* and *Prevotella* cleavage products includes contacting the *Eggerthella* cleavage product with a first FRET cassette comprising a first fluorescent label and a first quencher, and contacting the *Prevotella* cleavage product with a second FRET cassette comprising a second fluorescent label and a second quencher, where each FRET cassette hybridizes with the respective cleavage product so as to form a second *Eggerthella* or *Prevotella* cleavage structure capable of being cleaved by the flap endonuclease. If the *Eggerthella* cleavage product is present, the first fluorescent label is released from the first FRET cassette comprising the first quencher, and if the *Prevotella* cleavage product is present, the second fluorescent label is released from the second FRET cassette comprising the second quencher. The released first and/or second fluorescent label is then detected. In some variations utilizing first and second FRET cassettes, the first quencher and the second quencher are the same. In some particular embodiments, the *Eggerthella* cleavage product includes the sequence shown in residues 1-11 of SEQ ID NO:4, where residue 11 of SEQ ID NO:4 corresponds to the 3' terminal end of said cleavage product, and where the first FRET cassette optionally includes the sequence shown in SEQ ID NO:14; and/or the *Prevotella* cleavage product includes the sequence shown in residues 1-11 of SEQ ID NO:7, where residue 11 of SEQ ID NO:7 corresponds to the 3' terminal end of said cleavage product, and where the second FRET cassette optionally includes the sequence shown in SEQ ID NO:15.

In other embodiments of a method for diagnosing BV as above, the detection of *Eggerthella* and *Prevotella* includes, for each target, comparing a detection signal to a predetermined detection threshold for the target.

In some embodiments of a method for diagnosing BV in a subject, the assay for the detection of select bacterial species in each of the genera *Eggerthella* and *Prevotella* in the sample further detects select *Lactobacillus* species in the subject but does not detect *L. iners*. In such embodiments, if *Lactobacillus* is not detected, then the detection of at least one of *Eggerthella* and *Prevotella* indicates BV in the subject, and if *Lactobacillus* is detected, then the detection of both *Eggerthella* and *Prevotella* indicates BV in the subject.

In certain embodiments of a method comprising the detection of *Eggerthella*, *Prevotella*, and *Lactobacillus* as above, the assay for detection of *Eggerthella*, *Prevotella*, and *Lactobacillus* is a nucleic-acid-based detection assay. In some such embodiments, the nucleic-acid-based detection assay targets the 16S rRNA of *Eggerthella*, *Prevotella*, and *Lactobacillus*. In particular variations, the nucleic-acid-based detection assay targets (i) an *Eggerthella* 16S rRNA region corresponding to nucleotide positions 615 to 679 of SEQ ID NO:1, (ii) a *Prevotella* 16S rRNA region corresponding to nucleotide positions 954 to 1037 of SEQ ID NO:2, and/or (iii) a *Lactobacillus* 16S rRNA region corresponding to nucleotide positions 837 to 944 of SEQ ID NO:3. In other embodiments, the nucleic-acid-based detection assay is a non-amplification-based assay such as, for example, a cleavage-based assay. In some such embodiments, the cleavage-based assay detects an RNA target nucleic acid and utilizes a flap endonuclease that is capable of cleaving an RNA:DNA linear duplex structure; in other embodiments, the cleavage-based assay detects a DNA target nucleic acid and utilizes a flap endonuclease that is capable of cleaving a DNA:DNA linear duplex structure. In some variations of a method employing a nucleic-acid-based detection assay, the detection of *Eggerthella*, *Prevotella*, and *Lactobacillus* is performed using a homogeneous detection reaction. The detection of *Eggerthella*, *Prevotella*, and *Lactobacillus* may further be performed in real time.

In some embodiments of a method utilizing a cleavage-based assay for detection of *Eggerthella*, *Prevotella*, and *Lactobacillus*, the assay includes the following steps:

(i) contacting the sample with (A) an *Eggerthella*-specific primer that specifically hybridizes to a target sequence within SEQ ID NO:1, (B) a *Prevotella*-specific primer that specifically hybridizes to a target sequence within SEQ ID NO:2, and (C) a *Lactobacillus*-specific primer that specifically hybridizes to a target sequence within SEQ ID NO:3, where the contacting is performed under reaction conditions whereby each primer specifically hybridizes to its respective 16S rRNA target sequence within an *Eggerthella* target 16S rRNA, a *Prevotella* target 16S rRNA, or a *Lactobacillus* target 16S rRNA, if present;

(ii) providing reactions conditions whereby the 3' end of each hybridized primer is extended, thereby generating a single-stranded cDNA having a sequence complementary to a region of the *Eggerthella*, *Prevotella*, or *Lactobacillus* target 16S rRNA, the region located 5' to the respective primer target sequence;

(iii) contacting any *Eggerthella*, *Prevotella*, or *Lactobacillus* cDNA from step (ii) with (A) a first *Eggerthella* probe oligonucleotide having a 3' portion that specifically hybridizes to a first target sequence within the *Eggerthella* cDNA and a 5' portion that does not specifically hybridize to the *Eggerthella* cDNA, (B) a first *Prevotella* probe oligonucleotide having a 3' portion that specifically hybridizes to a first target sequence within the *Prevotella* cDNA and a 5' portion that does not specifically hybridize to the *Prevotella* cDNA, (C) a *Lactobacillus* probe oligonucleotide having a 3' portion that specifically hybridizes to a first target sequence within the *Lactobacillus* cDNA and a 5' portion that does not specifically hybridize to the *Lactobacillus* cDNA, (D) a second *Eggerthella* probe oligonucleotide having a 5' portion that specifically hybridizes to a second target sequence with the *Eggerthella* cDNA, where the second *Eggerthella* cDNA target sequence is located 3' and adjacent to the first *Eggerthella* cDNA target sequence, (E) a second *Prevotella* probe oligonucleotide having a 5' portion that specifically hybridizes to a second target sequence with the *Prevotella* cDNA, where the second *Prevotella* cDNA target sequence is located 3' and adjacent to the first *Prevotella* cDNA target sequence, and (F) a second *Lactobacillus* probe oligonucleotide having a 5' portion that specifically hybridizes to a second target sequence with the *Lactobacillus* cDNA, where the second *Lactobacillus* cDNA target sequence is located 3' and adjacent to the first *Lactobacillus* cDNA target sequence, where the contacting is performed under reaction conditions whereby if the *Eggerthella* cDNA is present, the first and second *Eggerthella* probe oligonucleotides stably hybridize to the *Eggerthella* cDNA so as to form an *Eggerthella* linear duplex cleavage structure, if the *Prevotella* cDNA is present, the first and second *Prevotella* probe oligonucleotides stably hybridize to the *Prevotella* cDNA so as to form a *Prevotella* linear duplex cleavage structure, and if the *Lactobacillus* cDNA is present, the first and second *Lactobacillus* probe oligonucleotides stably hybridize to the *Lactobacillus* cDNA so as to form a *Lactobacillus* linear duplex cleavage structure;

(iv) contacting the sample with a flap endonuclease capable of cleaving any cleavage structure from step (iii) under reaction conditions whereby if the *Eggerthella* cleavage structure is present, cleavage of the *Eggerthella* cleavage structure occurs to generate a *Eggerthella* cleavage product comprising the 5' portion of the first *Eggerthella* probe oligonucleotide, if the *Prevotella* cleavage structure is present, cleavage of the *Prevotella* cleavage structure occurs to generate a *Prevotella* cleavage product comprising the 5' portion of the first *Prevotella* probe oligonucleotide, and if the *Lactobacillus* cleavage structure is present, cleavage of the *Lactobacillus* cleavage structure occurs to generate a *Lactobacillus* cleavage product comprising the 5' portion of the first *Lactobacillus* probe oligonucleotide; and (v) detecting the presence or absence of the *Eggerthella*, *Prevotella*, or *Lactobacillus* cleavage products.

In some variations of a method comprising a cleavage-based assay for detection of *Eggerthella*, *Prevotella*, and *Lactobacillus* as above, any one or more of the following conditions is present: the *Eggerthella*-specific primer comprises the sequence shown in SEQ ID NO:6; the *Prevotella*-specific primer comprises the sequence shown in SEQ ID NO:9; the *Lactobacillus*-specific primer comprises the sequence shown in SEQ ID NO:13; the 3' portion of the first *Eggerthella* probe oligonucleotide comprises the sequence shown in residues 11-27 of SEQ ID NO:4; the 3' portion of the first *Prevotella* probe oligonucleotide comprises the sequence shown in residues 11-25 of SEQ ID NO:7; the 3' portion of the first *Lactobacillus* probe oligonucleotide comprises the sequence shown in residues 11-27 of SEQ ID NO:10; the 5' portion of the second *Eggerthella* probe oligonucleotide comprises the sequence shown in residues 1-20 of SEQ ID NO:5; the 5' portion of the second *Prevotella* probe oligonucleotide comprises the sequence shown in residues 1-24 of SEQ ID NO:8; and/or the 5' portion of the second *Lactobacillus* probe oligonucleotide comprises a sequence selected from the group consisting of (1) the sequence shown in residues 1-27 of SEQ ID NO:11 and (2) the sequence shown in residues 1-32 of SEQ ID NO:12.

In certain embodiments of a method comprising a cleavage-based assay for detection of *Eggerthella*, *Prevotella*, and *Lactobacillus* as above, detecting the *Eggerthella*, *Prevotella*, and *Lactobacillus* cleavage products includes contacting the *Eggerthella* cleavage product with a first FRET cassette comprising a first fluorescent label and a first quencher, contacting the *Prevotella* cleavage product with a second FRET cassette comprising a second fluorescent label and a second quencher, and contacting the *Lactobacillus* cleavage product with a third FRET cassette comprising a third fluorescent label and a third quencher, where each FRET cassette hybridizes with the respective cleavage product so as to form a second *Eggerthella*, *Prevotella*, or *Lactobacillus* cleavage structure capable of being cleaved by the flap endonuclease. If the *Eggerthella* cleavage product is present, the first fluorescent label is released from the first FRET cassette comprising the first quencher; if the *Prevotella* cleavage product is present, the second fluorescent label is released from the second FRET cassette comprising the second quencher; and if the *Lactobacillus* cleavage product is present, the third fluorescent label is released from the third FRET cassette comprising the third quencher. The released first, second, or third fluorescent label is then detected. In some variations utilizing first, second, and third FRET cassettes, the first quencher, the second quencher, and the third quencher are the same. In some particular embodiments, the *Eggerthella* cleavage product includes the sequence shown in residues 1-11 of SEQ ID NO:4, where residue 11 of SEQ ID NO:4 corresponds to the 3' terminal end of said cleavage product, and where the first FRET cassette optionally includes the sequence shown in SEQ ID NO:14; the *Prevotella* cleavage product includes the sequence shown in residues 1-11 of SEQ ID NO:7, where residue 11 of SEQ ID NO:7 corresponds to the 3' terminal end of said cleavage product, and where the second FRET cassette optionally includes the sequence shown in SEQ ID NO:15; and/or the *Lactobacillus* cleavage product includes the sequence shown in residues 1-11 of SEQ ID NO:10, where residue 11 of SEQ ID NO:10 corresponds to the 3' terminal end of said cleavage product, and where the third FRET cassette optionally includes the sequence shown in SEQ ID NO:16.

In certain embodiments of a method for diagnosing BV as above, the method includes the detection of no more than ten bacterial genera associated with BV. For example, in some embodiments, the method includes the detection of no more than five bacterial genera associated with BV, or the method does not include detection of bacterial genera associated with BV other than *Eggerthella*, *Prevotella*, and *Lactobacillus*.

In some embodiments of a method for diagnosing BV as above, if BV is indicated in the subject, then the method further includes administering a treatment regime for BV to the subject. In certain embodiments, the method is a method for monitoring BV in the subject and the subject is undergoing a treatment regime for BV prior to step (a); in some such variations, if BV is indicated in the subject, then the method further includes either (i) administering the treatment regime for BV to the subject (i.e., continuing to administer to same treatment regime administered to the subject prior to step (a)) or (ii) administering a different treatment regime for BV to the subject.

In other embodiments of a method for diagnosing BV and comprising the detection of *Eggerthella*, *Prevotella*, and *Lactobacillus* as above, the detection of *Eggerthella*, *Prevotella*, and *Lactobacillus* includes, for each target, comparing a detection signal to a predetermined detection threshold for the target.

In another aspect, the present invention provides a reaction mixture for detection of an *Eggerthella* target nucleic acid and a *Prevotella* target nucleic acid. The reaction mixture generally includes an *Eggerthella*-specific oligonucleotide that specifically hybridizes to a target sequence within a target nucleic acid of an *Eggerthella* species characterized by the presence of a 16S rRNA gene having a nucleobase sequence that is at least 98% identical (e.g., at least 99% or 100% identical) to the sequence shown in SEQ ID NO:1, but does not specifically hybridize to a sequence within a nucleic acid from other *Eggerthella* species, and a *Prevotella*-specific oligonucleotide that specifically hybridizes to a target sequence within a target nucleic acid of *P. amnii*, *P. disiens*, and *P. bivia*, but does not specifically hybridize to a sequence within a nucleic acid from other *Prevotella* species.

In some embodiments of a reaction mixture as above, the *Eggerthella* and *Prevotella* target nucleic acids are 16S rRNAs of *Eggerthella* and *Prevotella*, respectively. For example, in some embodiments, (i) the *Eggerthella*-specific oligonucleotide targets a sequence within an *Eggerthella* 16S rRNA region corresponding to nucleotide positions 615 to 679, and/or (ii) the *Prevotella*-specific oligonucleotide targets a sequence within a *Prevotella* 16S rRNA region corresponding to nucleotide positions 954 to 1037 of SEQ ID NO:2. Particularly suitable oligonucleotides targeting an *Eggerthella* 16S rRNA region corresponding to nucleotide positions 615 to 679 include an oligonucleotide comprising a target-hybridizing sequence substantially corresponding to the sequence shown in SEQ ID NO:6, an oligonucleotide comprising a target-hybridizing sequence substantially corresponding to the sequence shown in residues 11-27 of SEQ ID NO:4, and an oligonucleotide comprising a target-hybridizing sequence substantially corresponding to the sequence shown in residues 1-20 of SEQ ID NO:5. Particularly suitable oligonucleotides targeting a sequence within a *Prevotella* 16S rRNA region corresponding to nucleotide positions 954 to 1037 of SEQ ID NO:2 include an oligonucleotide comprising a target-hybridizing sequence substantially corresponding to the sequence shown in SEQ ID NO:9, an oligonucleotide comprising a target-hybridizing sequence substantially corresponding to the sequence shown in residues 11-25 of SEQ ID NO:7, and an oligonucleotide comprising a target-hybridizing sequence substantially corresponding to the sequence shown in residues 1-24 of SEQ ID NO:8. In certain embodiments of a reaction mixture as above, the mixture includes (a) at least two oligonucleotides that specifically hybridize to two different target sequences within the *Eggerthella* target nucleic acid (e.g., at least three oligonucleotides that specifically hybridize to at least three different *Eggerthella* target sequences), and/or (b) at least two oligonucleotides that specifically hybridize to two different target sequences within the *Prevotella* target nucleic acid (e.g., at least three oligonucleotide that specifically hybridize to at least three different *Prevotella* target sequences).

In some embodiments, a reaction mixture for detection of an *Eggerthella* target nucleic acid and a *Prevotella* target nucleic acid includes a *Lactobacillus*-specific oligonucleotide that specifically hybridizes to a target sequence within a target nucleic acid of *Lactobacillus* species, but does not specifically hybridize to a sequence within a nucleic acid from *L. iners*. In certain variations, the *Eggerthella*, *Prevotella*, and *Lactobacillus* target nucleic acids are 16S rRNAs of *Eggerthella*, *Prevotella*, and *Lactobacillus*, respectively. For example, in some embodiments, (i) the *Eggerthella*-specific oligonucleotide targets a sequence within an *Eggerthella* 16S rRNA region corresponding to nucleotide positions 615 to 679, (ii) the *Prevotella*-specific oligonucleotide targets a sequence within a *Prevotella* 16S rRNA region corresponding to nucleotide positions 954 to 1037 of SEQ ID NO:2, and/or (iii) the *Lactobacillus*-specific oligonucleotide targets a sequence within a *Lactobacillus* 16S rRNA region corresponding to nucleotide positions 837 to 944 of SEQ ID NO:3. Particularly suitable oligonucleotides targeting a sequence within an *Eggerthella* 16S rRNA region corresponding to nucleotide positions 615 to 679 include an oligonucleotide comprising a target-hybridizing sequence substantially corresponding to the sequence shown in SEQ ID NO:6, an oligonucleotide comprising a target-hybridizing sequence substantially corresponding to the sequence shown in residues 11-27 of SEQ ID NO:4, and an oligonucleotide comprising a target-hybridizing sequence substantially corresponding to the sequence shown in residues 1-20 of SEQ ID NO:5. Particularly suitable oligonucleotides targeting a sequence within a *Prevotella* 16S rRNA region corresponding to nucleotide positions 954 to 1037 of SEQ ID NO:2 include an oligonucleotide comprising a target-hybridizing sequence substantially corresponding to the sequence shown in SEQ ID NO:9, an oligonucleotide comprising a target-hybridizing sequence substantially corresponding to the sequence shown in residues 11-25 of SEQ ID NO:7, and an oligonucleotide comprising a target-hybridizing sequence substantially corresponding to the sequence shown in residues 1-24 of SEQ ID NO:8. Particularly suitable oligonucleotides targeting a sequence within a *Lactobacillus* 16S rRNA region corresponding to nucleotide positions 837 to 944 of SEQ ID NO:3 include an oligonucleotide comprising a target-hybridizing sequence substantially corresponding to the sequence shown in SEQ ID NO:13, an oligonucleotide comprising a target-hybridizing sequence substantially corresponding to the sequence shown in residues 11-27 of SEQ ID NO:10, an oligonucleotide comprising a target-hybridizing sequence substantially corresponding to the sequence shown in residues 1-27 of SEQ ID NO:11, and an oligonucleotide comprising a target-hybridizing sequence substantially corresponding to the sequence shown in residues 1-32 of SEQ ID NO:12. In certain embodiments of a reaction mixture as above, the mixture includes (a) at least two oligonucleotides that specifically hybridize to two different target sequences within the *Eggerthella* target nucleic acid (e.g., at least three oligonucleotides that specifically hybridize to at least three different *Eggerthella* target sequences), (b) at least two oligonucleotide that specifically hybridize to two different target sequences within the *Prevotella* target nucleic acid (e.g., at least three oligonucleotide that specifically hybridize to at least three different *Prevotella* target sequences), and/or (c) at at least two oligonucleotide that specifically hybridize to two different target sequences within the *Lactobacillus* target nucleic acid (e.g., at least three oligonucleotide that specifically hybridize to at least three different *Lactobacillus* target sequences).

These and other aspects of the invention will become evident upon reference to the following detailed description of the invention and the attached drawings.

Definitions

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

The terms "a," "an," and "the" include plural referents, unless the context clearly indicates otherwise. For example, "a nucleic acid" as used herein is understood to represent one or more nucleic acids. As such, the terms "a" (or "an"), "one or more," and "at least one" can be used interchangeably herein.

"Sample" includes any specimen that may contain *Eggerthella*, *Prevotella*, or *Lactobacillus* or components thereof, such as nucleic acids or fragments of nucleic acids. Samples include "biological samples" which include any tissue or material derived from a living or dead human that may contain *Eggerthella*, *Prevotella*, or *Lactobacillus* or components thereof (e.g., a target nucleic acid derived therefrom), including, e.g., vaginal swab samples, cervical brush samples, respiratory tissue or exudates such as bronchoscopy, bronchoalveolar lavage (BAL) or lung biopsy, sputum, saliva, peripheral blood, plasma, serum, lymph node, gastrointestinal tissue, feces, urine, semen or other body fluids or materials. The biological sample may be treated to physically or mechanically disrupt tissue or cell structure, thus releasing intracellular components into a solution which may further contain enzymes, buffers, salts, detergents and the like, which are used to prepare, using standard methods, a biological sample for analysis. Also, samples may include processed samples, such as those obtained from passing samples over or through a filtering device, or following centrifugation, or by adherence to a medium, matrix, or support.

Reference to the genera "*Eggerthella*," "*Prevotella*," or "*Lactobacillus*" herein, in the particular context as targets for detection to diagnose BV in a method of the present disclosure, and unless the context clearly dictates otherwise, is understood to mean the detection of select species from these genera in accordance with the present disclosure, specifically (i) for *Eggerthella*, an uncultured species of *Eggerthella* but not other *Eggerthella* species, where the uncultured *Eggerthella* species being characterized by the presence of a 16S rRNA gene having a nucleobase sequence that is at least 98% identical (e.g., at least 98.5%, at least 99%, at least 99.5% or 100% identical) to the sequence shown in SEQ ID NO:1; (ii) for *Prevotella*, *P. amnii*, *P. disiens*, and *P bivia*, but not other *Prevotella* species; and (iii) for *Lactobacillus*, any *Lactobacillus* species except *L. iners*.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see, e.g., International Patent Application Pub. No. WO 95/32305), phosphorothioate linkages, methylphosphonate linkages, or combinations thereof. Sugar moieties of the nucleic acid may be either ribose or deoxyribose, or similar compounds having known substitutions such as, for example, 2'-methoxy substitutions and 2'-halide substitutions (e.g., 2'-F). Nitrogenous bases may be conventional bases (A, G, C, T, U), analogs thereof (e.g., inosine, 5-methylisocytosine, isoguanine; see, e.g., *The Biochemistry of the Nucleic Acids* 5-36, Adams et al., ed., 11th ed., 1992; Abraham et al., 2007, *BioTechniques* 43: 617-24), which include derivatives of purine or pyrimidine bases (e.g., $N^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, $O^6$-methylguanine, 4-thio-pyrimidines, 4-amino-pyrimidines, 4-dimethylhydrazine-pyrimidines, and $O^4$-alkyl-pyrimidines, and pyrazolo-compounds, such as unsubstituted or 3-substituted pyrazolo [3,4-d]pyrimidine; U.S. Pat. Nos. 5,378,825, 6,949,367 and International Patent Application Pub. No. WO 93/13121, each incorporated by reference herein). Nucleic acids may include "abasic" residues in which the backbone does not include a nitrogenous base for one or more residues (see, e.g., U.S. Pat. No. 5,585,481, incorporated by reference herein). A nucleic acid may comprise only conventional sugars, bases, and linkages as found in RNA and DNA, or may include conventional components and substitutions (e.g., conventional bases linked by a 2'-methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., *Biochemistry* 43:13233-41, 2004, incorporated by reference herein). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well-known in the art although nucleic acids may be purified from natural sources using routine techniques.

The term "polynucleotide," as used herein, denotes a nucleic acid chain. Throughout this application, nucleic acids are designated by the 5'-terminus to the 3'-terminus. Standard nucleic acids, e.g., DNA and RNA, are typically synthesized "5'-to-3'," i.e., by the addition of nucleotides to the 3'-terminus of a growing nucleic acid.

A "nucleotide," as used herein, is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me).

A "non-nucleotide unit," as used herein, is a unit that does not significantly participate in hybridization of a polymer. Such units must not, for example, participate in any significant hydrogen bonding with a nucleotide, and would exclude units having as a component one of the five nucleotide bases or analogs thereof.

A "nucleic-acid-based detection assay," as used herein, is an assay for the detection of a target sequence within a target nucleic acid and utilizing one more oligonucleotides that specifically hybridize to the target sequence.

In certain embodiments in accordance with the present invention, a nucleic-acid-based detection assay is an "amplification-based assay," i.e., an assay that utilizes one or more steps for amplifying a nucleic acid target sequence. Various amplification methods for use in detection assays are known in the art, several of which are summarized further herein. For the sake of clarity, an amplification-based assay may include one or more steps that do not amplify a target sequence, such as, for example, steps used in non-amplification-based assay methods (e.g., a hybridization assay or a cleavage-based assay).

In other embodiments, a nucleic-acid-based detection assay is a "non-amplification-based assay," i.e., an assay that does not rely on any step for amplifying a nucleic acid target sequence. For the sake of clarity, a nucleic-acid-based detection assay that includes a reaction for extension of a primer in the absence of any corresponding downstream amplification oligomer (e.g., extension of a primer by a reverse transcriptase to generate an RNA:DNA duplex followed by an RNase digestion of the RNA, resulting in a single-stranded cDNA complementary to an RNA target but without generating copies of the cDNA) is understood to be a non-amplification-based assay.

An exemplary non-amplification-based assay is a "cleavage-based assay," which is an assay that relies on the specific cleavage, by a flap endonuclease, of a linear duplex cleavage structure formed by the specific hybridization of overlapping oligonucleotides to a target nucleic acid. In these assays, a probe oligonucleotide containing a non-target-hybridizing flap region is cleaved in an overlap-dependent manner by the flap endonuclease to release a cleavage product that is then detected. The principles of cleavage-based assays are well-known in the art, and exemplary assays are described in, for example, Lyamichev et al. (*Nat. Biotechnol.* 17:292-296, 1999), Ryan et al. (*Mol. Diagn.* 4:135-144, 1999), Allawi et al. (*J. Clin. Microbiol.* 44:3443-3447, 2006), U.S. Pat. Nos. 5,846,717 & 6,706,471 to Brow et al., and U.S. Pat. No. 5,614,402 to Dahlberg et al. Cleavage-based assays include, e.g., the commercially available Invader® assays (Hologic, Inc., Madison, Wis.).

When at least a region of a first oligonucleotide and at least a region of a second, different oligonucleotide anneal to different regions of the same linear complementary nucleic acid sequence, and the 3' end of the annealed region of the second oligonucleotide points toward or is adjacent to the 5' end of the annealed region of the first oligonucleotide, the second oligonucleotide may be called the "upstream" oligonucleotide and the first oligonucleotide the "downstream" oligonucleotide.

The term "cleavage structure," as used herein, refers to a structure that is formed by the interaction of a probe oligonucleotide and a target nucleic acid to form a duplex, where the resulting structure is cleavable by a flap endonuclease. The cleavage structure is a substrate for specific cleavage by the flap endonuclease, in contrast to a nucleic acid molecule that is a substrate for non-specific cleavage by agents such as phosphodiesterases, which cleave nucleic acid molecules without regard to secondary structure (i.e., no formation of a duplex structure is required).

A "flap endonuclease," as used herein, refers to a class of nucleolytic enzymes that act as structure-specific 5' endonucleases on nucleic acid structures with a duplex containing a single-stranded 5' overhang, or flap, on one of the strands that is displaced by another strand of nucleic acid (i.e., such that there are overlapping nucleotides where the adjacent first and second probes hybridize to a target). A flap endonuclease may also be referred to as a "5' endonuclease" or by the acronym "FEN" for short. FENs catalyze hydrolytic cleavage of the phosphodiester bond at the junction of single- and double-stranded nucleic acid, releasing the overhang, or flap. FENs are reviewed by Ceska and Savers (*Trends Biochem. Sci.* 23:331-336, 1998) and Liu et al. (*Annu. Rev. Biochem.* 73:589-615, 2004). A flap endonuclease is not restricted to enzymes having solely 5' nuclease activity. For example, the flap endonuclease may be a native DNA polymerase having 5' nuclease activity (e.g., Taq DNA polymerase, *E. coli* DNA polymerase I) or a modified DNA polymerase having 5' nuclease activity by lacking synthetic activity (e.g., a Cleavase® enzyme).

An "overlap region" consists of the base or bases of the first probe oligonucleotide that hybridize to the target and are overlapped by the second probe oligonucleotide. The base on the 3' end of the second probe oligonucleotide determines the end of the overlap region and may or may not hybridize to the target.

A "first probe oligonucleotide," in reference to a cleavage-based detection assay, refers to an oligonucleotide that interacts with a target nucleic acid to form a cleavage structure in the presence of a "second probe oligonucleotide" that hybridizes to a region upstream of the first probe oligonucleotide. When annealed to the target nucleic acid, the first probe oligonucleotide and target form a cleavage structure and cleavage by a flap endonuclease can occur within the first probe oligonucleotide. In the presence of an overlapping second probe oligonucleotide upstream of the first probe oligonucleotide along the target nucleic acid, the site of cleavage within the first probe oligonucleotide will occur after the last overlapping base (cleavage depends on at least one overlapping base of the second probe with target-hybridized bases of the first probe). In addition to a target-hybridizing region that hybridizes to a target sequence within the target nucleic acid, a first probe oligonucleotide contains a non-target-hybridizing region at the 5' end (also referred to as a "flap region"). When first and second probe oligonucleotides are annealed to a target nucleic acid, site-specific cleavage by a flap endonuclease occurs to generate a cleavage product that contains the flap region and the overlap region of the first probe oligonucleotide.

A "second probe oligonucleotide," in reference to a cleavage-based detection assay, refers to an oligonucleotide that contains a sequence at its 3' end that, when annealed to the target nucleic acid, overlaps the 5' end of the target-hybridizing sequence within a downstream first probe oligonucleotide; typically, these regions will compete for hybridization to the same segment along a complementary target nucleic acid. The 3' terminal nucleotide of the second probe oligonucleotide may or may not base pair with a nucleotide in the target nucleic acid. In some variations, only the 3' terminal nucleotide overlaps the 5' end of the target-hybridizing sequence of the first probe oligonucleotide.

As used herein, the term "FRET cassette" refers to a hairpin oligonucleotide that contains a fluorophore moiety and a nearby quencher moiety that quenches the fluorophore. Hybridization of a cleavage product with a FRET cassette produces a secondary substrate for the flap endonuclease. Once this substrate is formed, the 5' fluorophore-containing base is cleaved from the cassette, thereby generating a fluorescence signal.

A "target nucleic acid," as used herein, is a nucleic acid comprising a target sequence to be detected. Target nucleic acids may be DNA or RNA as described herein, and may be either single-stranded or double-stranded. The target nucleic acid may include other sequences besides the target sequence.

By "isolated" it is meant that a sample containing a target nucleic acid is taken from its natural milieu, but the term does not connote any degree of purification.

The term "target sequence," as used herein, refers to the particular nucleotide sequence of a target nucleic acid that is to be detected. The "target sequence" includes the complexing sequences to which oligonucleotides (e.g., probe oligonucleotide, priming oligonucleotides and/or promoter oligonucleotides) complex during a detection process (e.g., an amplification-based detection assay such as, for example, TMA or PCR, or a non-amplification-based detection assay such as, for example, a 5'-endonucleose-based assay). Where the target nucleic acid is originally single-stranded, the term "target sequence" will also refer to the sequence complementary to the "target sequence" as present in the target nucleic acid. Where the target nucleic acid is originally double-stranded, the term "target sequence" refers to both the sense (+) and antisense (−) strands. In choosing a target sequence, the skilled artisan will understand that a "unique" sequence should be chosen so as to distinguish between unrelated or closely related target nucleic acids.

"Target-hybridizing sequence" is used herein to refer to the portion of an oligomer that is configured to hybridize with a target nucleic acid sequence. Preferably, the target-hybridizing sequences are configured to specifically hybridize with a target nucleic acid sequence. Target-hybridizing sequences may be 100% complementary to the portion of the target sequence to which they are configured to hybridize; but not necessarily. Target-hybridizing sequences may also include inserted, deleted and/or substituted nucleotide residues relative to a target sequence. Less than 100% complementarity of a target-hybridizing sequence to a target sequence may arise, for example, when the target nucleic acid is a plurality strains within a species, such as would be the case for an oligomer configured to hybridize to the various strains of *Lactobacillus*, but not *L. iners*, or configured to hybridize to *P. amnii, P. disiens* and *P. bivia* species of *Prevotella*. It is understood that other reasons exist for configuring a target-hybridizing sequence to have less than 100% complementarity to a target nucleic acid.

Oligomer target-hybridizing sequences defined herein by reference to a specific sequence (e.g., by reference a region within SEQ ID NO:1, 2, or 3) are also understood to include functional complements thereof, unless the context clearly dictates otherwise. Thus, for example, where a target-hybridizing regions of an oligomer is defined by reference to a specific sequence corresponding to a target nucleic acid, it is understood that the oligomer may include a functional oligomer having a target-hybridizing sequence that is the complement of the specific reference sequence. Or where an oligomer is defined by its configuration to hybridize to a specific sequence, it is understood that the oligomer may include a functional oligomer having a target-hybridizing sequence that is configured to hybridize to the complement of the specific reference sequence.

The term "targets a sequence," as used herein in reference to a region of *Eggerthella, Prevotella*, or *Lactobacillus* nucleic acid, refers to a process whereby an oligonucleotide hybridizes to the target sequence in a manner that allows for detection as described herein. In one embodiment, the oligonucleotide is complementary with the targeted *Eggerthella, Prevotella*, or *Lactobacillus* nucleic acid sequence and contains no mismatches. In another embodiment, the oligonucleotide is complementary but contains 1, 2, 3, 4, or 5 mismatches with the targeted *Eggerthella, Prevotella*, or *Lactobacillus* nucleic acid sequence. Preferably, the oligonucleotide that hybridizes to the target nucleic acid sequence includes at least 10 to as many as 50 nucleotides complementary to the target sequence. It is understood that at least 10 and as many as 50 is an inclusive range such that 10, 50 and each whole number there between are included. Preferably, the oligomer specifically hybridizes to the target sequence.

The term "configured to" denotes an actual arrangement of the polynucleotide sequence configuration of a referenced oligonucleotide target-hybridizing sequence. For example, oligonucleotides that are configured to specifically hybridize to a target sequence have a polynucleotide sequence that specifically hybridizes to the referenced sequence under stringent hybridization conditions.

The term "configured to specifically hybridize to" as used herein means that the target-hybridizing region of an oligonucleotide is designed to have a polynucleotide sequence that could target a sequence of the referenced *Eggerthella, Prevotella*, or *Lactobacillus* target region. Such an oligonucleotide is not limited to targeting that sequence only, but is rather useful as a composition, in a kit or in a method for targeting a *Eggerthella, Prevotella*, or *Lactobacillus* target nucleic acid. The oligonucleotide is designed to function as a component of an assay for detection of *Eggerthella, Prevotella*, or *Lactobacillus* from a sample, and therefore is designed to target *Eggerthella, Prevotella*, or *Lactobacillus* in the presence of other nucleic acids commonly found in testing samples. "Specifically hybridize to" does not mean exclusively hybridize to, as some small level of hybridization to non-target nucleic acids may occur, as is understood in the art. Rather, "specifically hybridize to" means that the oligonucleotide is configured to function in an assay to primarily hybridize the target so that an accurate detection of target nucleic acid in a sample can be determined. The term "configured to" denotes an actual arrangement of the polynucleotide sequence configuration of the oligonucleotide target-hybridizing sequence.

The term "fragment," as used herein in reference to an *Eggerthella, Prevotella*, or *Lactobacillus* targeted nucleic acid, refers to a piece of contiguous nucleic acid. In certain embodiments, the fragment includes contiguous nucleotides from an *Eggerthella, Prevotella*, or *Lactobacillus* 16S ribosomal RNA, wherein the number of 16S contiguous nucleotides in the fragment are less than that for the entire 16S.

The term "region," as used herein, refers to a portion of a nucleic acid wherein said portion is smaller than the entire nucleic acid. For example, when the nucleic acid in reference is an oligonucleotide promoter primer, the term "region" may be used refer to the smaller promoter portion of the entire oligonucleotide. Similarly, and also as example only, when the nucleic acid is a 16S ribosomal RNA, the term "region" may be used to refer to a smaller area of the nucleic acid, wherein the smaller area is targeted by one or more oligonucleotides of the invention. As another non-limiting example, when the nucleic acid in reference is an amplicon, the term region may be used to refer to the smaller nucleotide sequence identified for hybridization by the target-hybridizing sequence of a probe.

The interchangeable terms "oligomer," "oligo," and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources or may be synthesized using any of a variety of well-known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase; it may function as a primer and provide a promoter if it contains a sequence recognized by an RNA polymerase and allows for transcription (e.g., a T7 Primer); and it may function to detect a target nucleic acid if it is capable of hybridizing to the target nucleic acid, or an amplicon thereof, and further provides a detectible moiety (e.g., an acridinium-ester compound).

As used herein, an oligonucleotide "substantially corresponding to" a specified reference nucleic acid sequence means that the oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. One skilled in the art will understand that "substantially corresponding oligonucleotides" can vary from a reference sequence and still hybridize to the same target nucleic acid sequence. It is also understood that a first nucleic acid corresponding to a second nucleic acid includes the RNA and DNA thereof and includes the complements thereof, unless the context clearly dictates otherwise. This variation from the nucleic acid may be stated in terms of a percentage of identical bases within the sequence or the percentage of perfectly complementary bases between the probe or primer and its target sequence. Thus, in certain embodiments, an oligonucleotide "substantially corresponds" to a reference nucleic acid sequence if these percentages of base identity or complementarity are from 100% to about 80%. In preferred embodiments, the percentage is from 100% to about 85%. In more preferred embodiments, this percentage is from 100% to about 90%; in other preferred embodiments, this percentage is from 100% to about 95%. Similarly, a region of a nucleic acid or amplified nucleic acid can be referred to herein as corresponding to a reference nucleic acid sequence. One skilled in the art will understand the various modifications to the hybridization conditions that might be required at various percentages of complementarity to allow hybridization to a specific target sequence without causing an unacceptable level of non-specific hybridization.

An "amplification oligomer" is an oligomer, at least the 3'-end of which is complementary to a target nucleic acid, and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is an oligomer that is not extended by a polymerase (e.g., because it has a 3' blocked end) but participates in or facilitates amplification. For example, the 5' region of an amplification oligonucleotide may include a promoter sequence that is non-complementary to the target nucleic acid (which may be referred to as a "promoter primer" or "promoter provider"). Those skilled in the art will understand that an amplification oligomer that functions as a primer may be modified to include a 5' promoter sequence, and thus function as a promoter primer. Incorporating a 3' blocked end further modifies the promoter primer, which is now capable of hybridizing to a target nucleic acid and providing an upstream promoter sequence that serves to initiate transcription, but does not provide a primer for oligo extension. Such a modified oligo is referred to herein as a "promoter provider" oligomer. Size ranges for amplification oligonucleotides include those that are about 10 to about 70 nt long (not including any promoter sequence or poly-A tails) and contain at least about 10 contiguous bases, or even at least 12 contiguous bases that are complementary to a region of the target nucleic acid sequence (or a complementary strand thereof). The contiguous bases are at least 80%, or at least 90%, or completely complementary to the target sequence to which the amplification oligomer binds. An amplification oligomer may optionally include modified nucleotides or analogs, or additional nucleotides that participate in an amplification reaction but are not complementary to or contained in the target nucleic acid, or template sequence. It is understood that when referring to ranges for the length of an oligonucleotide, amplicon, or other nucleic acid, that the range is inclusive of all whole numbers (e.g., 19-25 contiguous nucleotides in length includes 19, 20, 21, 22, 23, 24 & 25).

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter provider" or "provider" refers to an oligonucleotide comprising first and second regions, and which is modified to prevent the initiation of DNA synthesis from its 3'-terminus. The "first region" of a promoter provider oligonucleotide comprises a base sequence which hybridizes to a DNA template, where the hybridizing sequence is situated 3', but not necessarily adjacent to, a promoter region. The hybridizing portion of a promoter oligonucleotide is typically at least 10 nucleotides in length, and may extend up to 50 or more nucleotides in length. The "second region" comprises a promoter sequence for an RNA polymerase. A promoter oligonucleotide is engineered so that it is incapable of being extended by an RNA- or DNA-dependent DNA polymerase, e.g., reverse transcriptase, preferably comprising a blocking moiety at its 3'-terminus as described above. As referred to herein, a "T7

Provider" is a blocked promoter provider oligonucleotide that provides an oligonucleotide sequence that is recognized by T7 RNA polymerase.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (see, e.g., U.S. Pat. No. 4,786,600, incorporated by reference herein). PCR amplification uses a DNA polymerase, pairs of primers, and thermal cycling to synthesize multiple copies of two complementary strands of dsDNA or from a cDNA (see, e.g., U.S. Pat. Nos. 4,683,195; 4,683,202; and 4,800,159; each incorporated by reference herein). LCR amplification uses four or more different oligonucleotides to amplify a target and its complementary strand by using multiple cycles of hybridization, ligation, and denaturation (see, e.g., U.S. Pat. Nos. 5,427,930 and 5,516,663, each incorporated by reference herein). SDA uses a primer that contains a recognition site for a restriction endonuclease and an endonuclease that nicks one strand of a hemimodified DNA duplex that includes the target sequence, whereby amplification occurs in a series of primer extension and strand displacement steps (see, e.g., U.S. Pat. Nos. 5,422,252; 5,547,861; and 5,648,211; each incorporated by reference herein).

"Transcription-associated amplification" or "transcription-mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods and single-primer transcription associated amplification method are embodiments of amplification-based assay methods used for detection of *Eggerthella*, *Prevotella*, or *Lactobacillus* target sequences as described herein. Variations of transcription-associated amplification are well known in the art as previously disclosed in detail (see, e.g., U.S. Pat. Nos. 4,868,105; 5,124,246; 5,130,238; 5,399,491; 5,437,990; 5,554,516; and 7,374,885; and International Patent Application Pub. Nos. WO 88/01302; WO 88/10315; and WO 95/03430; each incorporated by reference herein). The person of ordinary skill in the art will appreciate that the disclosed compositions may be used in amplification methods based on extension of oligomer sequences by a polymerase.

The term "amplicon" or the term "amplification product," as used herein, refers to the nucleic acid molecule generated during an amplification procedure that is complementary or homologous to a sequence contained within the target sequence. The complementary or homologous sequence of an amplicon is sometimes referred to herein as a "target-specific sequence." Amplicons generated using the amplification oligomers of the current invention may comprise non-target specific sequences. Amplicons can be double stranded or single stranded and can include DNA, RNA or both. For example, DNA-dependent RNA polymerase transcribes single stranded amplicons from double-stranded DNA during transcription-mediated amplification procedures. These single-stranded amplicons are RNA amplicons and can be either strand of a double-stranded complex, depending on how the amplification oligomers are configured. Thus, amplicons can be single-stranded RNA. RNA-dependent DNA polymerases synthesize a DNA strand that is complementary to an RNA template. Thus, amplicons can be double-stranded DNA and RNA hybrids. RNA-dependent DNA polymerases often include RNase activity, or are used in conjunction with an RNase, which degrades the RNA strand. Thus, amplicons can be single stranded DNA. RNA-dependent DNA polymerases and DNA-dependent DNA polymerases synthesize complementary DNA strands from DNA templates. Thus, amplicons can be double-stranded DNA. RNA-dependent RNA polymerases synthesize RNA from an RNA template. Thus, amplicons can be double-stranded RNA. DNA-dependent RNA polymerases synthesize RNA from double-stranded DNA templates, also referred to as transcription. Thus, amplicons can be single stranded RNA. Amplicons and methods for generating amplicons are known to those skilled in the art. For convenience herein, a single strand of RNA or a single strand of DNA may represent an amplicon generated by an amplification oligomer combination of the current invention. Such representation is not meant to limit the amplicon to the representation shown. Skilled artisans in possession of the instant disclosure will use amplification oligomers and polymerase enzymes to generate any of the numerous types of amplicons, all within the spirit and scope of the current invention.

A "non-target-specific sequence," as used herein, refers to a region of an oligomer sequence, wherein said region does not stably hybridize with a target sequence under standard hybridization conditions. One example of an oligomer with a non-target-specific sequence is a probe oligonucleotide for use in a cleavage-based assay as described herein, where the probe oligonucleotide includes a 5' "flap" region that is not complementary to the target or target sequence. Other oligomers with non-target-specific sequences include, but are not limited to, promoter primers and molecular beacons. An amplification oligomer may contain a sequence that is not complementary to the target or template sequence; for example, the 5' region of a primer may include a promoter sequence that is non-complementary to the target nucleic acid (referred to as a "promoter primer"). Those skilled in the art will understand that an amplification oligomer that functions as a primer may be modified to include a 5' promoter sequence, and thus function as a promoter primer. Similarly, a promoter primer may be modified by removal of, or synthesis without, a promoter sequence and still function as a primer. A 3' blocked amplification oligomer may provide a promoter sequence and serve as a template for polymerization (referred to as a "promoter provider"). Thus, an amplicon that is generated by an amplification oligomer member such as a promoter primer will comprise a target-specific sequence and a non-target-specific sequence.

"Detection probe," "detection oligonucleotide," and "detection probe oligomer" are used interchangeably to refer to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Detection probes may be DNA, RNA, analogs thereof or combinations thereof and they may be labeled or unlabeled. Detection probes may further include alternative backbone linkages such as, e.g., 2'-O-methyl linkages. A detection probe's "target sequence" generally refers to a smaller nucleic acid sequence region within a larger nucleic acid sequence that hybridizes specifically to at least a portion of a probe oligomer by standard base pairing. A detection probe may comprise target-specific sequences and other sequences that contribute to the three-dimensional conformation of the probe (see, e.g., U.S. Pat. Nos. 5,118,801; 5,312,728; 6,849, 412; 6,835,542; 6,534,274; and 6,361,945; and US Patent Application Pub. No. 20060068417; each incorporated by reference herein).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g., hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (see, e.g., U.S. Pat. Nos. 5,283,174; 5,656,207; and 5,658,737; each incorporated by reference herein). Labels include chemiluminescent compounds, e.g., acridinium ester ("AE") compounds that include standard AE and derivatives (see, e.g., U.S. Pat. Nos. 5,656,207; 5,658,737; and 5,639,604; each incorporated by reference herein). Synthesis and methods of attaching labels to nucleic acids and detecting labels are well known. (See, e.g., Sambrook et al., *Molecular Cloning, A Laboratory Manual,* 2nd ed. (Cold Spring Harbor Laboratory Press, Cold Spring Harbor, N Y, 1989), Chapter 10, incorporated by reference herein. See also U.S. Pat. Nos. 5,658,737; 5,656,207; 5,547,842; 5,283,174; and 4,581,333; each incorporated by reference herein). More than one label, and more than one type of label, may be present on a particular probe, or detection may use a mixture of probes in which each probe is labeled with a compound that produces a detectable signal (see, e.g., U.S. Pat. Nos. 6,180,340 and 6,350,579, each incorporated by reference herein).

"Capture probe," "capture oligonucleotide," and "capture probe oligomer" are used interchangeably to refer to a nucleic acid oligomer that specifically hybridizes to a target sequence in a target nucleic acid by standard base pairing and joins to a binding partner on an immobilized probe to capture the target nucleic acid to a support. One example of a capture oligomer includes two binding regions: a sequence-binding region (e.g., target-specific portion) and an immobilized probe-binding region, usually on the same oligomer, although the two regions may be present on two different oligomers joined together by one or more linkers. Another embodiment of a capture oligomer uses a target-sequence binding region that includes random or non-random poly-GU, poly-GT, or poly U sequences to bind non-specifically to a target nucleic acid and link it to an immobilized probe on a support.

As used herein, an "immobilized oligonucleotide," "immobilized probe," or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g., G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues, including abasic residues that are not complementary. Sufficiently complementary contiguous sequences typically are at least 80%, or at least 90%, complementary to a sequence to which an oligomer is intended to specifically hybridize. Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary (see, e.g., Sambrook et al., *Molecular Cloning, A Laboratory Manual,* $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein). It is understood that ranges for percent identity are inclusive of all whole and partial numbers (e.g., at least 90% includes 90, 91, 93.5, 97.687 and etc.).

By "preferentially hybridize" or "specifically hybridize" is meant that under stringent hybridization assay conditions, probes hybridize to their target sequences, or replicates thereof, to form stable probe:target hybrids, while at the same time formation of stable probe:non-target hybrids is minimized Thus, a probe hybridizes to a target sequence or replicate thereof to a sufficiently greater extent than to a non-target sequence, to enable one having ordinary skill in the art to accurately detect the target sequence or replicates thereof. Appropriate hybridization conditions are well-known in the art, may be predicted based on sequence composition, or can be determined by using routine testing methods (see, e.g., Sambrook et al., *Molecular Cloning, A Laboratory Manual*, $2^{nd}$ ed. (Cold Spring Harbor Laboratory Press, Cold Spring Harbor, N.Y., 1989) at §§ 1.90-1.91, 7.37-7.57, 9.47-9.51 and 11.47-11.57, particularly §§ 9.50-9.51, 11.12-11.13, 11.45-11.47 and 11.55-11.57, incorporated by reference herein).

By "nucleic acid hybrid," "hybrid," or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or method that treats a sample for subsequent detection of *Eggerthella*, *Prevotella*, or *Lactobacillus* or components thereof present in the sample. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of a nucleic acid oligonucleotide that selectively or non-specifically capture a target nucleic acid and separate it from other sample components (e.g., as described in U.S. Pat. No. 6,110,678 and International Patent Application Pub. No. WO 2008/016988, each incorporated by reference herein).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of a sample component from other sample components.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T7, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. A primer is required to initiate synthesis with both RNA and DNA templates.

As used herein, a "reaction mixture" is a mixture of reagents that are capable of reacting together to produce a product in appropriate external conditions over a period of time. A reaction mixture man contain, for example, amplification assay reagents, hybridization assay reagents, and/or cleavage-based assay reagents, the recipes for which are independently known in the art.

As used herein, a "colony-forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, a "treatment regime," in the context of a subject diagnosed with BV, refers to a combination of amount of a therapeutic agent administered to the subject and dosage frequency.

BRIEF DESCRIPTION OF THE DRAWINGS

FIG. 1 illustrates a reference sequence for *Eggerthella* 16S ribosomal RNA gene (SEQ ID NO:1; uncultured bacterium clone rRNA250 16S ribosomal RNA gene, partial sequence, found at GenBank under accession number AY959023.1 GI:66878729).

FIG. 2 illustrates a reference sequence for *Prevotella* 16S ribosomal RNA gene (SEQ ID NO:2: *Prevotella bivia* strain SEQ195 16S ribosomal RNA gene, partial sequence, found at GenBank under accession number JN867270.1 GI:359550828).

FIG. 3 illustrates a reference sequence for *Lactobacillus* 16S ribosomal RNA gene (SEQ ID NO:3: *Lactobacillus crispatus* ST1 complete genome, strain ST1, found at GenBank under accession number FN692037.1 GI:295029968).

DETAILED DESCRIPTION

Figure 4:
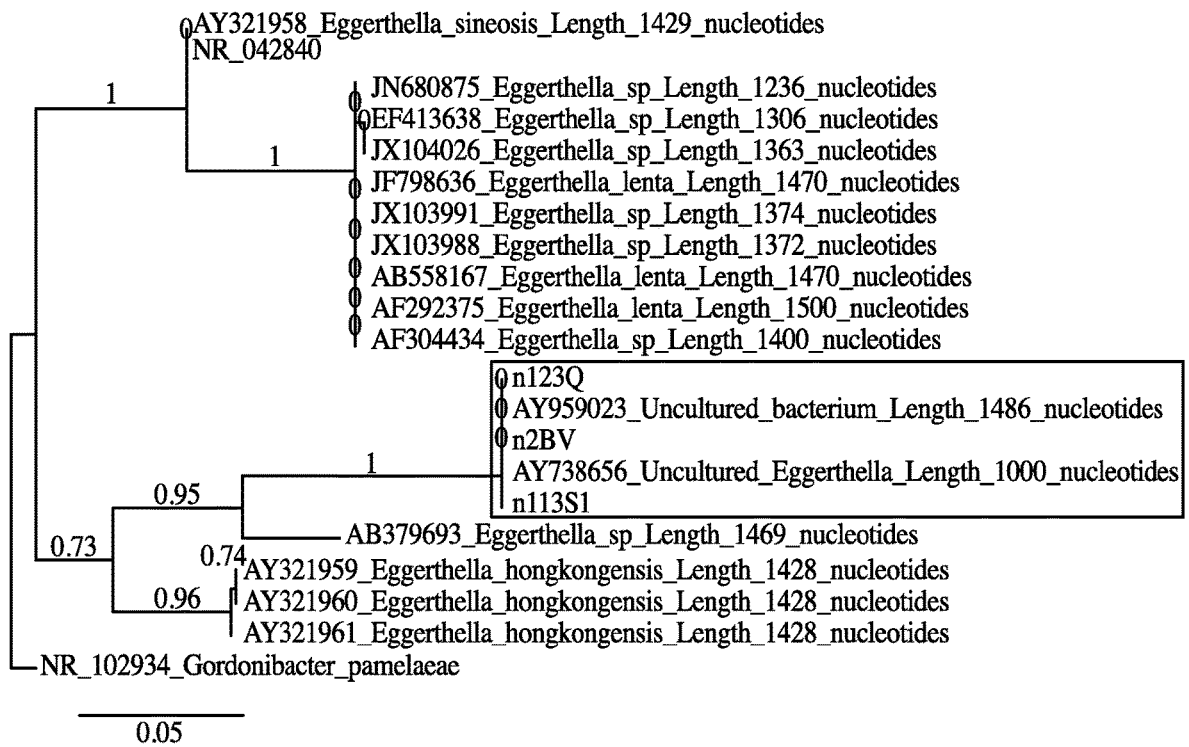
FIG. 4 is a phylogram indicating targeted species of the genus *Eggerthella*. Sequences obtained from uncultured species of *Eggerthella* were targeted and are indicated by the box. The phylogram was constructed using the maximum likelihood method with a bootstrap value of 100. The number at each branch choice indicates the frequency of the branch choice.

The present invention provides methods and compositions for diagnosing Bacterial Vaginosis (BV) in a subject. The methods exploit highly-specific, low abundance anaerobic bacteria belonging to the genera *Eggerthella* and *Prevotella*. The methods generally include detecting the presence or absence of select bacterial species in each of these genera in a sample from a subject suspected of having BV. In particular, an assay is performed for the specific detection in the sample of an uncultured species of *Eggerthella* but not other *Eggerthella* species, the uncultured *Eggerthella* species being characterized by the presence of a 16S rRNA gene having a nucleobase sequence that is at least 98% identical to the sequence shown in SEQ ID NO:1, and an assay for the specific detection in the sample of *P. amnii*, *P. disiens*, and *P bivia*, but not other *Prevotella* species. Utilizing these species-specific assays, the detection of at least one of *Eggerthella* and *Prevotella* in the sample is generally indicative of BV in the subject, with greater sensitivity and specificity than some existing tests.

The performance of the *Eggerthella/Prevotella* combination for diagnosing BV can be improved by the inclusion of *Lactobacillus* as an indicator of vaginal health. Accordingly, in some embodiments, the method further includes detecting the presence or absence of select species of *Lactobacillus*. In particular, an assay is performed for the specific detection in the sample of *Lactobacillus* species, where the assay does not detect *L. iners*. In these embodiments, if *Lactobacillus* is not detected, then the detection of either *Eggerthella* or *Prevotella* indicates BV in the subject, and if *Lactobacillus* is detected, then the detection of both *Eggerthella* and *Prevotella* indicates BV in the subject. As described further herein, an exemplary assay using this combination of bacterial targets and logic yielded a test that was 95.6% sensitive and 97.3% specific when compared to the Nugent Score.

In some embodiments, the uncultured *Eggerthella* species is characterized by the presence of a 16S rRNA gene having a nucleobase sequence that is at least 98.5%, at least 99%, at least 99.5%, at least 99.6%, at least 99.7%, at least 99.8%, at least 99.9%, or 100% identical to the sequence shown in SEQ ID NO:1. Typically, the 16S rRNA gene of the uncultured *Eggerthella* species has a region that is 100% identical to nucleotide positions 615 to 679 of SEQ ID NO:1.

While the select bacterial species from *Eggerthella*, *Prevotella*, and/or *Lactobacillus* may be detected using any suitable method, it is presently preferred that the select species are detected using a nucleic-acid-based detection assay. Nucleic-acid-based detection assays in accordance with the present invention generally utilize oligonucleotides that specifically hybridize to a target nucleic acid of the select species of *Eggerthella*, *Prevotella*, or *Lactobacillus* with minimal cross-reactivity to other nucleic acids suspected of being in a sample. As previously indicated, an assay to detect the uncultured *Eggerthella* species does not detect other *Eggerthella* species; an assay to detect *P. amnii*, *P. disiens*, and *P bivia* does not detect other *Prevotella* species; and an assay to detect *Lactobacillus* species does not detect *L. iners*. Accordingly, oligonucleotides for nucleic-acid-based detection of the select species of *Eggerthella*, *Prevotella*, or *Lactobacillus* will specifically hybridize to the target species within the respective genus with minimal cross-reactivity to non-target species. Additionally, oligonucleotides for nucleic-acid-based detection of the select species of *Eggerthella*, *Prevotella*, and *Lactobacillus* will have minimal cross-reactivity to species within other bacterial genera, including, for example, *Trichomonas* sp.; *Trichomonas vaginalis*; *Candida* sp.; Bacterium from the order Clostridiales; *Clostridium*-like sp.; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Megasphaera* sp.; *Leptotrichia sanguinegens*; and *Finegoldia magna*. In one aspect, a nucleic-acid-based detection assay in accordance with the present invention further includes components for detecting one of more of these organisms, or other bacterial genera associated with BV.

In particular embodiments, a nucleic-acid-based detection assay targets the 16S rRNA of *Eggerthella*, *Prevotella*, and/or *Lactobacillus*, or a gene encoding the 16S rRNA. Particularly suitable target regions of the 16S rRNA or the encoding gene are (i) an *Eggerthella* 16S rRNA region corresponding to nucleotide positions 615 to 679 of SEQ ID NO:1; (ii) a *Prevotella* 16S rRNA region corresponding to nucleotide positions 954 to 1037 of SEQ ID NO:2; and (iii) a *Lactobacillus* 16S rRNA region corresponding to nucleotide positions 837 to 944 of SEQ ID NO:3. In specific variations of a nucleic-acid-based detection assay targeting a 16S rRNA region as above, (a) an *Eggerthella*-specific oligonucleotide includes a target-hybridizing region comprising a sequence substantially corresponding to the sequence shown in SEQ ID NO:6, a sequence substantially corresponding to the sequence shown in residues 11-27 of SEQ ID NO:4, or a sequence substantially corresponding to the sequence shown in residues 1-20 of SEQ ID NO:5; (b) a *Prevotella*-specific oligonucleotide includes a target-hybridizing region comprising a sequence substantially corresponding to the sequence shown in SEQ ID NO:9, a sequence substantially corresponding to the sequence shown in residues 11-25 of SEQ ID NO:7, or a sequence substantially corresponding to the sequence shown in residues 1-24 of SEQ ID NO:8; and/or (c) a *Lactobacillus*-specific oligonucleotide includes a target-hybridizing region comprising a sequence substantially corresponding to the sequence shown in SEQ ID NO:13, a sequence substantially corresponding to the sequence shown in residues 11-27 of SEQ ID NO:10, a sequence substantially corresponding to the sequence shown in residues 1-27 of SEQ ID NO:11, or a sequence substantially corresponding to the sequence shown in residues 1-32s of SEQ ID NO:12. In some such embodiments, (a) an *Eggerthella*-specific oligonucleotide includes a target-hybridizing region comprising or consisting of the sequence shown in SEQ ID NO:6, the sequence shown in residues 11-27 of SEQ ID NO:4, or the sequence shown in residues 1-20 of SEQ ID NO:5; (b) a *Prevotella*-specific oligonucleotide includes a target-hybridizing region comprising or consisting of the sequence shown in SEQ ID NO:9, the sequence shown in residues 11-25 of SEQ ID NO:7, or the sequence shown in residues 1-24 of SEQ ID NO:8; and/or (c) a *Lactobacillus*-specific oligonucleotide includes a target-hybridizing region comprising or consisting of the sequence shown in SEQ ID NO:13, the sequence shown in residues 11-27 of SEQ ID NO:10, the sequence shown in residues 1-27 of SEQ ID NO:11, or the sequence shown in residues 1-32s of SEQ ID NO:12. In certain embodiments, a nucleic-acid-based detection assay utilizes at least two or three *Eggerthella*-specific oligonucleotides, at least two or three *Prevotella*-specific oligonucleotides, and/or at least two or three *Lactobacillus*-specific oligonucleotides, which may be oligonucleotides selected from those specified above.

In some embodiments of a method comprising the use of a nucleic-acid-base detection assay, an amplification-based assay is used to detect the select bacterial species of *Eggerthella, Prevotella*, and/or *Lactobacillus*. Such variations generally include amplifying a target sequence within a bacterial target nucleic acid utilizing an in vitro nucleic acid amplification reaction and detecting the amplified product by, for example, specifically hybridizing the amplified product with a nucleic acid detection probe that provides a signal to indicate the presence of a select bacterial species in the sample. The amplification step includes contacting the sample with two or more amplification oligomers specific for a target sequence in a target nucleic acid (e.g., a target sequence in a 16S rRNA) to produce an amplified product if the target nucleic acid is present in the sample. Amplification synthesizes additional copies of the target sequence or its complement by using at least one nucleic acid polymerase to extend the sequence from an amplification oligomer (a primer) using a template strand. One embodiment for detecting the amplified product uses a hybridizing step that includes contacting the amplified product with at least one probe specific for a sequence amplified by the selected amplification oligomers, e.g., a sequence contained in the target sequence flanked by a pair of selected primers. Suitable amplification methods include, for example, replicase-mediated amplification, polymerase chain reaction (PCR), ligase chain reaction (LCR), strand-displacement amplification (SDA), and transcription-mediated or transcription-associated amplification (TMA). Such amplification methods are well-known in the art (see, e.g., discussion of amplification methods in Definitions section, supra) and are readily used in accordance with the methods of the present invention.

For example, some amplification methods that use TMA amplification include the following steps. Briefly, the target nucleic acid that contains the sequence to be amplified is provided as single stranded nucleic acid (e.g., ssRNA or ssDNA). Those skilled in the art will appreciate that conventional melting of double stranded nucleic acid (e.g., dsDNA) may be used to provide single-stranded target nucleic acids. A promoter primer binds specifically to the target nucleic acid at its target sequence and a reverse transcriptase (RT) extends the 3' end of the promoter primer using the target strand as a template to create a cDNA copy of the target sequence strand, resulting in an RNA:DNA duplex. An RNase digests the RNA strand of the RNA:DNA duplex and a second primer binds specifically to its target sequence, which is located on the cDNA strand downstream from the promoter primer end. RT synthesizes a new DNA strand by extending the 3' end of the second primer using the first cDNA template to create a dsDNA that contains a functional promoter sequence. An RNA polymerase specific for the promoter sequence then initiates transcription to produce RNA transcripts that are about 100 to 1000 amplified copies ("amplicons") of the initial target strand in the reaction. Amplification continues when the second primer binds specifically to its target sequence in each of the amplicons and RT creates a DNA copy from the amplicon RNA template to produce an RNA:DNA duplex. RNase in the reaction mixture digests the amplicon RNA from the RNA:DNA duplex and the promoter primer binds specifically to its complementary sequence in the newly synthesized DNA. RT extends the 3' end of the promoter primer to create a dsDNA that contains a functional promoter to which the RNA polymerase binds to transcribe additional amplicons that are complementary to the target strand. The autocatalytic cycles of making more amplicon copies repeat during the course of the reaction resulting in about a billion-fold amplification of the target nucleic acid present in the sample. The amplified products may be detected in real-time during amplification, or at the end of the amplification reaction by using a probe that binds specifically to a target sequence contained in the amplified products. Detection of a signal resulting from the bound probes indicates the presence of the target nucleic acid in the sample.

In some embodiments, the method utilizes a "reverse" TMA reaction. In such variations, the initial or "forward" amplification oligomer is a priming oligonucleotide that hybridizes to the target nucleic acid in the vicinity of the 3'-end of the target region. A reverse transcriptase (RT) synthesizes a cDNA strand by extending the 3'-end of the primer using the target nucleic acid as a template. The second or "reverse" amplification oligomer is a promoter primer or promoter provider having a target-hybridizing sequence configure to hybridize to a target-sequence contained within the synthesized cDNA strand. Where the second amplification oligomer is a promoter primer, RT extends the 3' end of the promoter primer using the cDNA strand as a template to create a second, cDNA copy of the target sequence strand, thereby creating a dsDNA that contains a functional promoter sequence. Amplification then continues essentially as described above for initiation of transcription from the promoter sequence utilizing an RNA polymerase. Alternatively, where the second amplification oligomer is a promoter provider, a terminating oligonucleotide, which hybridizes to a target sequence that is in the vicinity to the 5'-end of the target region, is typically utilized to terminate extension of the priming oligomer at the 3'-end of the terminating oligonucleotide, thereby providing a defined 3'-end for the initial cDNA strand synthesized by extension from the priming oligomer. The target-hybridizing sequence of the promoter provider then hybridizes to the defined 3'-end of the initial cDNA strand, and the 3'-end of the cDNA strand is extended to add sequence complementary to the promoter sequence of the promoter provider, resulting in the formation of a double-stranded promoter sequence. The initial cDNA strand is then used a template to transcribe multiple RNA transcripts complementary to the initial cDNA strand, not including the promoter portion, using an RNA polymerase that recognizes the double-stranded promoter and initiates transcription therefrom. Each of these RNA transcripts is then available to serve as a template for further amplification from the first priming amplification oligomer.

In certain embodiments comprising an amplification-based detection assay, a combination of at least two amplification oligomers is utilized for the detection of an *Eggerthella* 16S rRNA or a gene encoding an *Eggerthella* 16S rRNA. The oligomer combination may include first and second amplification oligomers for amplifying an *Eggerthella* nucleic acid target region corresponding to SEQ ID NO:1 from about nucleotide position 615 to about nucleotide position 679. For example, in some embodiments, the first amplification oligomer includes a target-hybridizing region comprising a sequence substantially corresponding to the sequence shown in SEQ ID NO:6, and the second amplification oligomer includes a target-hybridizing region comprising a sequence substantially corresponding to the sequence shown in residues 11-27 of SEQ ID NO:4, or a sequence substantially corresponding to the sequence shown in residues 1-20 of SEQ ID NO:5. In more particular variations, the first amplification oligomer includes a target-hybridizing region comprising or consisting of the sequence shown in SEQ ID NO:6, and the second amplification oligomer includes a target-hybridizing region comprising or consisting of the sequence shown in residues 11-27 of SEQ ID NO:4, or comprising or consisting of the sequence shown in residues 1-20 of SEQ ID NO:5.

In certain embodiments comprising an amplification-based detection assay, a combination of at least two amplification oligomers is utilized for the detection of a *Prevotella* 16S rRNA or a gene encoding a *Prevotella* 16S rRNA. The oligomer combination may include first and second amplification oligomers for amplifying a *Prevotella* nucleic acid target region corresponding to SEQ ID NO:2 from about nucleotide position 954 to about nucleotide position 1034. For example, in some embodiments, the first amplification oligomer includes a target-hybridizing region comprising a sequence substantially corresponding to the sequence shown in SEQ ID NO:9, and the second amplification oligomer includes a target-hybridizing region comprising a sequence substantially corresponding to the sequence shown in residues 11-25 of SEQ ID NO:7, or a sequence substantially corresponding to the sequence shown in residues 1-24 of SEQ ID NO:8. In more particular variations, the first amplification oligomer includes a target-hybridizing region comprising or consisting of the sequence shown in SEQ ID NO:9, and the second amplification oligomer includes a target-hybridizing region comprising or consisting of the sequence shown in residues 11-25 of SEQ ID NO:7, or comprising or consisting of the sequence shown in residues 1-24 of SEQ ID NO:8.

In certain aspects comprising an amplification-based detection assay, a combination of at least two amplification oligomers is utilized for the detection of a *Lactobacillus* 16S rRNA or a gene encoding a *Lactobacillus* 16S rRNA. The oligomer combination may include first and second amplification oligomers for amplifying a *Lactobacillus* nucleic acid target region corresponding to SEQ ID NO:3 from about nucleotide position 837 to about nucleotide position 944. For example, in some embodiments, the first amplification oligomer includes a target-hybridizing region comprising a sequence substantially corresponding to the sequence shown in SEQ ID NO:13, and the second amplification oligomer includes a target-hybridizing region comprising a sequence substantially corresponding to the sequence shown in residues 11-27 of SEQ ID NO:10, a sequence substantially corresponding to the sequence shown in residues 1-27 of SEQ ID NO:11, or a sequence substantially corresponding to the sequence shown in residues 1-32 of SEQ ID NO:12. In more particular variations, the first amplification oligomer includes a target-hybridizing region comprising or consisting of the sequence shown in SEQ ID NO:13, and the second amplification oligomer includes a target-hybridizing region comprising or consisting of the sequence shown in residues 11-27 of SEQ ID NO:10, comprising or consisting of the sequence shown in residues 1-27 of SEQ ID NO:11, or comprising or consisting of the sequence shown in residues 1-32 of SEQ ID NO:12.

Detection of the amplified products may be accomplished by a variety of methods to detect a signal specifically associated with the amplified target sequence. The nucleic acids may be associated with a surface that results in a physical change, such as a detectable electrical change. Amplified nucleic acids may be detected by concentrating them in or on a matrix and detecting the nucleic acids or dyes associated with them (e.g., an intercalating agent such as ethidium bromide or cyber green), or detecting an increase in dye associated with nucleic acid in solution phase. Other methods of detection may use nucleic acid detection probes that are configured to specifically hybridize to a sequence in the amplified product and detecting the presence of the probe:product complex, or by using a complex of probes that may amplify the detectable signal associated with the amplified products (e.g., U.S. Pat. Nos. 5,424,413; 5,451,503; and 5,849,481; each incorporated by reference herein). Directly or indirectly labeled probes that specifically associate with the amplified product provide a detectable signal that indicates the presence of the target nucleic acid in the sample. For example, if the target nucleic acid is the 16S rRNA of *Eggerthella*, *Prevotella*, or *Lactobacillus*, the amplified product will contain a target sequence in or complementary to a sequence in the 16S rRNA, and a probe will bind directly or indirectly to a sequence contained in the amplified product to indicate the presence of the 16S rRNA of *Eggerthella*, *Prevotella*, or *Lactobacillus* in the tested sample.

Detection probes that hybridize to the complementary amplified sequences may be DNA or RNA oligomers, or oligomers that contain a combination of DNA and RNA nucleotides, or oligomers synthesized with a modified backbone, e.g., an oligomer that includes one or more 2'-methoxy substituted ribonucleotides. Probes used for detection of the amplified sequences may be unlabeled and detected indirectly (e.g., by binding of another binding partner to a moiety on the probe) or may be labeled with a variety of detectable labels. In some embodiments of the method for diagnosing BV, such as in certain embodiments using transcription-mediated amplification (TMA), the detection probe is a linear chemiluminescently labeled probe such as, e.g., a linear acridinium ester (AE) labeled probe.

The detection step may also provide additional information on the amplified sequence, such as, e.g., all or a portion of its nucleic acid base sequence. Detection may be performed after the amplification reaction is completed, or may be performed simultaneously with amplifying the target region, e.g., in real time. In one embodiment, the detection step allows homogeneous detection, e.g., detection of the hybridized probe without removal of unhybridized probe from the mixture (see, e.g., U.S. Pat. Nos. 5,639,604 and 5,283,174, each incorporated by reference herein).

In embodiments that detect the amplified product near or at the end of the amplification step, a linear detection probe may be used to provide a signal to indicate hybridization of the probe to the amplified product. One example of such detection uses a luminescently labeled probe that hybridizes to target nucleic acid. Luminescent label is then hydrolyzed from non-hybridized probe. Detection is performed by chemiluminescence using a luminometer. (see, e.g., International Patent Application Pub. No. WO 89/002476, incorporated by reference herein). In other embodiments that use real-time detection, the detection probe may be a hairpin probe such as, for example, a molecular beacon, molecular torch, or hybridization switch probe that is labeled with a reporter moiety that is detected when the probe binds to amplified product. Such probes may comprise target-hybridizing sequences and non-target-hybridizing sequences. Various forms of such probes have been described previously (see, e.g., U.S. Pat. Nos. 5,118,801; 5,312,728; 5,925,517; 6,150,097; 6,849,412; 6,835,542; 6,534,274; and 6,361,945; and US Patent Application Pub. Nos. 20060068417A1 and 20060194240A1; each incorporated by reference herein).

In some embodiments of a method comprising the use of a nucleic-acid-base detection assay, a non-amplification-based assay is used to detect the select bacterial species of *Eggerthella*, *Prevotella*, and/or *Lactobacillus*. In some such embodiments, the non-amplification-based assay is a hybridization assay comprising the hybridization of a specific detection probe to a target nucleic acid. Methods for conducting polynucleotide hybridization assays have been well developed in the art. Hybridization assay procedures and conditions will vary depending on the application and are selected in accordance with the general binding methods known, including those referred to in, e.g., Maniatis et al., *Molecular Cloning: A Laboratory Manual* (3rd ed. Cold Spring Harbor, N.Y., 2002), and Berger and Kimmel, Methods in Enzymology, Vol. 152, *Guide to Molecular Cloning Techniques* (Academic Press, Inc., San Diego, Calif., 1987). Generally, the probe and sample are mixed under conditions that will permit specific nucleic acid hybridization, and specific hybridization of the probe to its respective target is then detected. Nucleic acid hybridization is adaptable to a variety of assay formats. One suitable format is the sandwich assay format, which is particularly adaptable to hybridization under non-denaturing conditions. A primary component of a sandwich-type assay is a solid support, which has adsorbed to it or covalently coupled to it immobilized nucleic acid probe that is unlabeled and complementary to one portion of the DNA sequence. Target nucleic acid is hybridized to the immobilized probe, and a second, labeled detection probe—which is complementary to a second and different region of the same DNA strand to which the immobilized, unlabeled nucleic acid probe is hybridized—is hybridized to the [target nucleic acid]:[immobilized probe] duplex to detect the target nucleic acid. Another exemplary format utilizes electrochemical detection of target nucleic acids hybridized to unlabeled detection probes immobilized on a suitable electrode surface as a signal transducer. See, e.g., Drummond et al., *Nat. Biotechnol.* 21:1192, 2003; Gooding, *Electroanalysis* 14:1149, 2002; Wang, *Anal. Chim. Acta* 469:63, 2002; Cagnin et al., *Sensors* 9:3122, 2009; Katz and Willner, *Electroanalysis* 15:913, 2003; Daniels and Pourmand, *Electroanalysis* 19:1239, 2007.

In certain embodiments comprising a hybridization assay, a detection probe is utilized for the detection of an *Eggerthella*, *Prevotella*, and/or *Lactobacillus* 16S rRNA or a gene encoding an *Eggerthella*, *Prevotella*, and/or *Lactobacillus* 16S rRNA. In such embodiments, a probe for detecting an *Eggerthella* 16S rRNA or gene encoding an *Eggerthella* 16S rRNA specifically hybridizes to a nucleic acid target region corresponding to SEQ ID NO:1 from about nucleotide position 615 to about nucleotide position 679; a probe for detecting a *Prevotella* 16S rRNA or gene encoding a *Prevotella* 16S rRNA specifically hybridizes to a nucleic acid target region corresponding to SEQ ID NO:2 from about nucleotide position 954 to about nucleotide position 1034; and/or a probe for detecting a *Lactobacillus* 16S rRNA or gene encoding a *Lactobacillus* 16S rRNA specifically hybridizes to a nucleic acid target region corresponding to SEQ ID NO:3 from about nucleotide position 837 to about nucleotide position 944. For example, in some variations, a probe for detection of *Eggerthella* includes a target-hybridizing region comprising a sequence substantially corresponding to the sequence shown in SEQ ID NO:6, a sequence substantially corresponding to the sequence shown in residues 11-27 of SEQ ID NO:4, or a sequence substantially corresponding to the sequence shown in residues 1-20 of SEQ ID NO:5 (e.g., a target-hybridizing region comprising or consisting of the sequence shown in SEQ ID NO:6, residues 11-27 of SEQ ID NO:4, or residues 1-20 of SEQ ID NO:5). In some variations, a probe for detection of *Prevotella* includes a target-hybridizing region comprising a sequence substantially corresponding to the sequence shown in SEQ ID NO:9, a sequence substantially corresponding to the sequence shown in residues 11-25 of SEQ ID NO:7, or a sequence substantially corresponding to the sequence shown in residues 1-24 of SEQ ID NO:8 (e.g., a target-hybridizing region comprising or consisting of the sequence shown in SEQ ID NO:9, residues 11-25 of SEQ ID NO:7, or residues 1-24 of SEQ ID NO:8). In some variations, a probe for detection of *Lactobacillus* includes a target-hybridizing region comprising a sequence substantially corresponding to the sequence shown in SEQ ID NO:13, a sequence substantially corresponding to the sequence shown in residues 11-27 of SEQ ID NO:10, a sequence substantially corresponding to the sequence shown in residues 1-27 of SEQ ID NO:11, or a sequence substantially corresponding to the sequence shown in residues 1-32 of SEQ ID NO:12 (e.g., a target-hybridizing region comprising or consisting of the sequence shown in SEQ ID NO:13, residues 11-27 of SEQ ID NO:10, residues 1-27 of SEQ ID NO:11, or residues 1-32 of SEQ ID NO:12).

In some preferred embodiments, a non-amplification-based assay for detection of *Eggerthella*, *Prevotella*, and/or *Lactobacillus* is a cleavage-based assay, in which a probe oligonucleotide containing a non-target-hybridizing flap region is cleaved in an overlap-dependent manner by a flap endonuclease to release a cleavage product that is then detected. Exemplary cleavage-based assay reagents are described in, e.g., Lyamichev et al. (*Nat. Biotechnol.*

17:292-296, 1999), Ryan et al. (*Mol. Diagn.* 4:135-144, 1999), and Allawi et al. (*J. Clin. Microbiol.* 44:3443-3447, 2006). Appropriate conditions for flap endonuclease reactions are either known or can be readily determined using methods known in the art (see, e.g., Kaiser et al., *J. Biol. Chem.* 274:2138-721394, 1999). Exemplary flap endonucleases that may be used in the method include *Thermus aquaticus* DNA polymerase I, *Thermus thermophilus* DNA polymerase I, mammalian FEN-1, *Archaeoglobus fulgidus* FEN-1, *Methanococcus jannaschii* FEN-1, *Pyrococcus furiosus* FEN-1, *Methanobacterium thermoautotrophicum* FEN-1, *Thermus thermophilus* FEN-1, CLEAVASE® (Hologic, Inc., Madison, Wis.), *S. cerevisiae* RTH1, *S. cerevisiae* RAD27, *Schizosaccharomyces pombe* rad2, bacteriophage T5 5'-3' exonuclease, *Pyrococcus horikoshii* FEN-1, human endonuclease 1, calf thymus 5'-3' exonuclease, including homologs thereof in eubacteria, eukaryotes, and archaea, such as members of the class II family of structure-specific enzymes, as well as enzymatically active mutants or variants thereof. Descriptions of flap endonucleases can be found in, for example, Lyamichev et al., Science 260:778-783, 1993; Eis et al., *Nat. Biotechnol.* 19:673-676, 2001; Shen et al., *Trends in Bio. Sci.* 23:171-173, 1998; Kaiser et al., *J. Biol. Chem.* 274:21387-21394, 1999; Ma et al., *J. Biol. Chem.* 275:24693-24700, 2000; Allawi et al., *J. Mol. Biol.* 328: 537-554, 2003; Sharma et al., *J. Biol. Chem.* 278:23487-23496, 2003; and Feng et al., *Nat. Struct. Mol. Biol.* 11:450-456, 2004.

In certain variations, a cleavage-based assay detects an RNA target nucleic acid of *Eggerthella, Prevotella*, and/or *Lactobacillus*, and the cleavage-based assay utilizes a flap endonuclease that is capable of cleaving and RNA:DNA linear duplex structure. In some alternative embodiments, a cleavage-based assay detects a DNA target nucleic acid of *Eggerthella, Prevotella*, and/or *Lactobacillus*, and the cleavage-based assay utilizes a flap endonuclease that is capable of cleaving and DNA:DNA linear duplex structure. Exemplary flap endonucleases capable of cleaving RNA:DNA duplexes include polymerase-deficient 5' nucleases of the genus *Thermus* as well as certain CLEAVASE® enzymes (Hologic, Inc., Madison, Wis.) such as, for example, CLEAVASE® BN (BstX-NotI deletion of Taq polymerase, see U.S. Pat. No. 5,614,402), CLEAVASE® II ("AG" mutant of full length Taq polymerase, see U.S. Pat. No. 5,614,402), CLEAVASE® VII (synthesis-deficient mutation of full length *Thermus thermophilus* polymerase), CLEAVASE® IX (polymerase deficient mutant of the Tth DNA polymerase), and CLEAVASE® XII (polymerase deficient chimeric polymerase constructed from fragments of taq DNA polymerase and Tth DNA polymerase). Exemplary flap endonucleases capable of cleaving DNA:DNA duplexes include the flap endonucleases indicated above, as well as CLEAVASE® 2.0 (*Archaeoglobus fulgidus* FEN-1), CLEAVASE® 2.1 (*Archaeoglobus fulgidus* FEN-1 with 6 histidines on the C-terminus), CLEAVASE® 3.0 (*Archaeoglobus veneficus* FEN-1), and CLEAVASE® 3.1 (*Archaeoglobus veneficus* FEN-1 with 6 histidines on the C-terminus).

In some embodiments, a cleavage-based assay detects an RNA target nucleic acid of *Eggerthella, Prevotella*, and/or *Lactobacillus*, and the assay includes a step for synthesizing a DNA complement of an RNA target region, which cDNA strand is then hybridized to overlapping first and second probe oligonucleotides to form a linear duplex cleavage structure for cleavage by the flap endonuclease. Reaction conditions for synthesizing cDNA from an RNA template, using an RNA-dependent DNA polymerase (reverse transcriptase), are well-known in the art.

In some embodiments, a cleavage-based assay targets an *Eggerthella, Prevotella*, and/or *Lactobacillus* 16S rRNA or a gene encoding an *Eggerthella, Prevotella*, and/or *Lactobacillus* 16S rRNA. In certain variations, a cleavage-based assay targets (i) an *Eggerthella* 16S rRNA region corresponding to nucleotide positions 615 to 679 of SEQ ID NO:1, (ii) a *Prevotella* 16S rRNA region corresponding to nucleotide positions 954 to 1037 of SEQ ID NO:2, and/or (iii) a *Lactobacillus* 16S rRNA region corresponding to nucleotide positions 837 to 944 of SEQ ID NO:3.

For example, in certain embodiments of a cleavage-based assay targeting an *Eggerthella* 16S rRNA target region, utilizing overlapping first and second oligonucleotides, the first probe oligonucleotide includes a target-hybridizing region substantially corresponding to the sequence shown in residues 11-27 of SEQ ID NO:4 and/or the second probe oligonucleotide includes a target-hybridizing region substantially corresponding to the sequence shown in residues 1-20 of SEQ ID NO:5. In some variations, a reverse transcriptase reaction is performed to synthesize a cDNA copy of the 16S rRNA, such as, for example, a reverse transcriptase reaction utilizing a primer having a target-hybridizing region substantially corresponding to the sequence shown in SEQ ID NO:6. In more particular variations for the detection of *Eggerthella*, a first probe oligonucleotide includes a target-hybridizing region comprising or consisting of the sequence shown in residues 11-27 of SEQ ID NO:4; a second probe oligonucleotide includes a target-hybridizing region comprising or consisting of the sequence shown in residues 1-20 of SEQ ID NO:5; and/or a reverse transcriptase primer includes a target-hybridizing sequence comprising or consisting of the sequence shown in SEQ ID NO:6.

In some embodiments of a cleavage-based assay targeting an *Prevotella* 16S rRNA target region, utilizing overlapping first and second oligonucleotides, the first probe oligonucleotide includes a target-hybridizing region substantially corresponding to the sequence shown in residues 11-25 of SEQ ID NO:7 and/or the second probe oligonucleotide includes a target-hybridizing region substantially corresponding to the sequence shown in residues 1-24 of SEQ ID NO:8. In some variations, a reverse transcriptase reaction is performed to synthesize a cDNA copy of the 16S rRNA, such as, for example, a reverse transcriptase reaction utilizing a primer having a target-hybridizing region substantially corresponding to the sequence shown in SEQ ID NO:9. In more particular variations for the detection of *Prevotella*, a first probe oligonucleotide includes a target-hybridizing region comprising or consisting of the sequence shown in residues 11-25 of SEQ ID NO:7; a second probe oligonucleotide includes a target-hybridizing region comprising or consisting of the sequence shown in residues 1-24 of SEQ ID NO:8; and/or a reverse transcriptase primer includes a target-hybridizing sequence comprising or consisting of the sequence shown in SEQ ID NO:9.

In some embodiments of a cleavage-based assay targeting an *Lactobacillus* 16S rRNA target region, utilizing overlapping first and second oligonucleotides, the first probe oligonucleotide includes a target-hybridizing region substantially corresponding to the sequence shown in residues 11-27 of SEQ ID NO:10 and/or the second probe oligonucleotide includes a target-hybridizing region substantially corresponding to a sequence selected from the sequence shown in residues 1-27 of SEQ ID NO:11 and the sequence shown is residues 1-32 of SEQ ID NO:12. In some variations, a reverse transcriptase reaction is performed to synthesize a cDNA copy of the 16S rRNA, such as, for example, a reverse transcriptase reaction utilizing a primer having a target-hybridizing region substantially corresponding to the sequence shown in SEQ ID NO:13. In more particular variations for the detection of *Lactobacillus*, a first probe oligonucleotide includes a target-hybridizing region comprising or consisting of the sequence shown in residues 11-27 of SEQ ID NO:10; a second probe oligonucleotide includes a target-hybridizing region comprising or consisting of a sequence selected from the sequence shown in residues 1-27 of SEQ ID NO:11 and the sequence shown is residues 1-32 of SEQ ID NO:12; and/or a reverse transcriptase primer includes a target-hybridizing sequence comprising or consisting of the sequence shown in SEQ ID NO:13.

In typical variations of a cleavage-based detection assay, a cleavage product is detected using a hairpin oligonucleotide probe known as a FRET cassette, which contains a fluorophore at its 5' end and a nearby quencher that quenches the fluorophore. Hybridization of the cleavage product with a FRET cassette produces a secondary substrate for the flap endonuclease, whereby the 5' fluorophore-containing base is cleaved from the cassette, thereby generating a fluorescence signal. Principles governing the design and construction of FRET cassettes for use in cleavage-based assays are well-known in the art, and these principles may be readily adapted by a skilled artisan for using such probes in accordance with certain embodiments of the present invention. In specific embodiments, (i) where an *Eggerthella* cleavage product comprises the sequence shown in residues 1-11 of SEQ ID NO:4 and residue 11 corresponds to the 3' terminal end of the cleavage product, a FRET cassette for detection of the *Eggerthella* cleavage product comprises or consists of the sequence shown in SEQ ID NO:14; (ii) where a *Prevotella* cleavage product comprises the sequence shown in residues 1-11 of SEQ ID NO:7 and residue 11 corresponds to the 3' terminal end of the cleavage product, a FRET cassette for detection of the *Prevotella* cleavage product comprises or consists of the sequence shown in SEQ ID NO:15; and/or (iii) where a *Lactobacillus* cleavage product comprises the sequence shown in residues 1-11 of SEQ ID NO:10 and residue 11 corresponds to the 3' terminal end of the cleavage product, a FRET cassette for detection of the *Lactobacillus* cleavage product comprises or consists of the sequence shown in SEQ ID NO:16. The secondary substrate formed by hybridization of a FRET cassette to an *Eggerthella* cleavage product, a *Prevotella* cleavage product, or a *Lactobacillus* cleavage product (each comprising a 5' portion of a first *Eggerthella* probe oligonucleotide, a first *Prevotella* probe oligonucleotide, or a first *Lactobacillus* probe oligonucleotide, respectively) is also referred to herein as a "second *Eggerthella* cleavage structure," a "second *Prevotella* cleavage structure," or a "second *Lactobacillus* cleavage structure," respectively. For the sake of clarity, the use of the term "second [*Eggerthella*, *Prevotella*, or *Lactobacillus*] cleavage structure" in this context is not meant to imply that a FRET cassette has any specificity for an *Eggerthella*, *Prevotella*, or *Lactobacillus* target sequence, since it is understood that the 5' portion of the corresponding first probe oligonucleotide does not itself hybridize to the respective target.

The assay for detection of *Eggerthella*, *Prevotella*, and/or *Lactobacillus* can include, for each target, comparing a detection signal to a predetermined detection threshold for each target. Thresholds for each target may be determined, for example, by analyzing samples from a population of women attending medical facilities and who have been scored for the presence of BV using, e.g., Nugent Scores and/or the Amsel Criteria. In such embodiments, samples are assayed to determine detection signals for each target, and a detection threshold is defined based on the observed separation between samples from subjects who have scored positive for BV and sample from subject who have scored negative for BV (e.g., the observed separation between Nugent positive and Nugent negative samples). For example, in some embodiments of the method utilizing a cleavage-based detection assay, a detection threshold is determined based on the initial rate of the FEN endonuclease reaction, which correlates with fluorescence signal generated from cleavage of a FRET cassette. Exemplary use of detection thresholds for determining the presence or absence of target bacteria, based on the initial reaction rate in a cleavage-based assay, is discussed further herein in Example 1.

In certain embodiments utilizing a nucleic-acid-based detection assay, the method further includes purifying the *Eggerthella*, *Prevotella*, and/or *Lactobacillus* target nucleic acid from other components in the sample. Such purification may include may include methods of separating and/or concentrating organisms contained in a sample from other sample components. In particular embodiments, purifying the target nucleic acid includes capturing the target nucleic acid to specifically or non-specifically separate the target nucleic acid from other sample components. Non-specific target capture methods may involve selective precipitation of nucleic acids from a substantially aqueous mixture, adherence of nucleic acids to a support that is washed to remove other sample components, or other means of physically separating nucleic acids from a mixture that contains *Eggerthella*, *Prevotella*, and/or *Lactobacillus* nucleic acid and other sample components.

In some embodiments, a target nucleic acid (e.g., a 16S rRNA target nucleic or a gene encoding the 16S rRNA) of *Eggerthella*, *Prevotella*, and/or *Lactobacillus* is separated from other sample components by hybridizing the target nucleic acid to a capture probe oligomer. The capture probe oligomer comprises a target-hybridizing sequence configured to specifically or non-specifically hybridize to a target nucleic acid so as to form a [target nucleic acid]:[capture probe] complex that is separated from other sample components. Capture probes comprising target-hybridizing sequences suitable for non-specific capture of target nucleic acids are described in, e.g., International PCT Publication WO 2008/016988, incorporated by reference herein. In a preferred variation, the capture probe binds the [target nucleic acid]:[capture probe] complex to an immobilized probe to form a [target nucleic acid]:[capture probe]—[immobilized probe] complex that is separated from the sample and, optionally, washed to remove non-target sample components (see, e.g., U.S. Pat. Nos. 6,110,678; 6,280,952; and 6,534,273; each incorporated by reference herein). In such variations, the capture probe oligomer further comprises a sequence or moiety that binds attaches the capture probe, with its bound target sequence, to an immobilized probe attached to a solid support, thereby permitting the hybridized target nucleic acid to be separated from other sample components.

In more specific embodiments, the capture probe oligomer includes a tail portion (e.g., a 3' tail) that is not complementary to target nucleic acid but that specifically hybridizes to a sequence on the immobilized probe, thereby serving as the moiety allowing the target nucleic acid to be separated from other sample components, such as previously described in, e.g., U.S. Pat. No. 6,110,678, incorporated herein by reference. Any sequence may be used in a tail region, which is generally about 5 to 50 nt long, and preferred embodiments include a substantially homopolymeric tail of about 10 to 40 nt (e.g., $A_{10}$ to $A_{40}$), more preferably about 14 to 33 nt (e.g., $A_{14}$ to $A_{30}$ or $T_3A_{14}$ to $T_3A_{30}$), that bind to a complementary immobilized sequence (e.g., poly-T) attached to a solid support, e.g., a matrix or particle.

Target capture typically occurs in a solution phase mixture that contains one or more capture probe oligomers that hybridize to the target nucleic acid under hybridizing conditions, usually at a temperature higher than the $T_m$, of the [tail sequence]:[immobilized probe sequence] duplex. For embodiments comprising a capture probe tail, the [target nucleic acid]:[capture probe] complex is captured by adjusting the hybridization conditions so that the capture probe tail hybridizes to the immobilized probe, and the entire complex on the solid support is then separated from other sample components. The support with the attached [immobilized probe]:[capture probe]:[target nucleic acid] may be washed one or more times to further remove other sample components. Preferred embodiments use a particulate solid support, such as paramagnetic beads, so that particles with the attached [target nucleic acid]:[capture probe]:[immobilized probe] complex may be suspended in a washing solution and retrieved from the washing solution, preferably by using magnetic attraction. In embodiments of the method comprising the use of an amplification-based detection assay, to limit the number of handling steps, a target nucleic acid may be amplified by simply mixing the target nucleic acid in the complex on the support with amplification oligomers and proceeding with amplification steps.

In some embodiments of a method for diagnosing BV, where detection of *Eggerthella* and/or *Prevotella* indicate BV in a subject, the method further includes treating BV in the subject. Treatment regimes for BV are generally known in the art and include, for example, administration of antibiotic drugs such as metronidazole (e.g., FLAGYL, METROGEL-VAGINAL), clindamycin (e.g., CLEOCIN, CLINDESSE), and tinidazole (e.g., TINDAMAX). In certain variations, the subject has not been previously diagnosed with BV. In other embodiments, the subject has been previously diagnosed with BV and is undergoing treatment for BV at the time a diagnostic method of the present disclosure is performed. Such variations are particularly useful for monitoring treatment of BV in a subject. For example, if the method indicates that BV is still present in the subject, then the subject may continue treatment. In some embodiments, the same treatment regime (i.e., the same treatment that the subject is undergoing at the time the present diagnostic method is performed) is re-administered to the subject. Alternatively, the continued presence of BV in the subject undergoing treatment may indicate that a change in the ongoing treatment is needed, and a different treatment regime (e.g., a different medication, or an increased dosage and/or frequency of a drug) is administered to the subject.

In accordance with the present invention, detecting the presence or absence of *Eggerthella* and *Prevotella*, or the presence or absence of *Eggerthella*, *Prevotella*, and *Lactobacillus*, may be performed separately for each target (e.g., in separate reaction vessels, sequentially or in parallel), or performed together as a multiplex reaction system. Accordingly, in some embodiments, a method for diagnosing BV utilizes a multiplex reaction, where the reaction mix contains reagents for assaying multiple (e.g., at least two, three, four, or more) different target sequences in parallel. In these cases, a reaction mix may contain multiple different target-specific oligonucleotides for performing the detection assay. For example, in a method utilizing an amplification-based detection assay, a multiplex reaction may contain multiple sets (e.g., multiple pairs) of amplification oligomers (for example, multiple pairs of PCR primers or multiple pairs of TMA amplification oligomers (e.g., for TMA, multiple pairs of promoter primer and non-promoter primer, or multiple pairs of promoter provider and non-promoter primer)). In other embodiments utilizing a cleavage-based detection assay, a multiplex reaction may contain multiple first probe oligonucleotides having different flaps, multiple different overlapping second probe oligonucleotides, and multiple different FRET cassettes for detecting the different flaps, once they are cleaved. Upon cleavage of the FRET cassettes, multiple distinguishable fluorescent signals may be observed. Compounds for fluorescently labeling oligonucleotides are well-known and publically available in the art, as are the various FRET and non-FRET techniques for preparing and using labeled oligonucleotides containing excitation and, optionally, quenching compounds (see e.g., Dyomics GmbH, Jena Germany; Glen Research Corporation, Sterling, Va.; Biosearch Technologies, Novato, Calif.).

Additional microbe detection assays can be similarly performed for determining the presence and/or relative amount of a plurality of microbes implicated in BV. By way of example only, such plurality of microbes can include one or more of anaerobic gram-positive cocci; *Trichomonas* sp.; *Trichomonas vaginalis*; *Candida* sp.; *Eggerthella* sp.; Bacterium from the order Clostridiales; *Clostridium*-like sp.; *Atopobium* sp.; *Atopobium vaginae*; Enterobacteria; *Peptostreptococcus micros*; *Aerococcus christensenii*; *Leptotrichia amnionii*; *Peptoniphilus* sp.; *Dialister* sp.; *Mycoplasma hominis*; *Sneathia sanguinegens*; *Anaerococcus tetradius*; *Mobiluncus* sp.; *Mobiluncus hominis*; *Eggerthella hongkongensis*; *Megasphaera* sp.; *Leptotrichia sanguinegens* and *Finegoldia magna*. Assays may be performed separately or multiplexed. Thus, a diagnosis of BV can include identifying a plurality of microbes and optionally determining their relative abundances in a sample.

In certain embodiments, the method for diagnosing BV includes the detection of no more than ten bacterial genera associated with BV. In other embodiments, the method includes the detection of no more than nine, no more than eight, no more than seven, no more than six, no more than five, or nor more than four bacterial genera associated with BV. In some variations, the method does not include detection of bacterial genera associated with BV other than *Eggerthella*, *Prevotella*, and/or *Lactobacillus*.

Also provided by the subject invention is a reaction mixture for detection of an *Eggerthella*, *Prevotella*, and/or *Lactobacillus* target nucleic acid. A reaction mixture in accordance with the present invention generally comprises an oligomer or oligomer combination as described herein for detection of select species of one or more of *Eggerthella*, *Prevotella*, and *Lactobacillus* target nucleic acid. The reaction mixture generally includes (i) an *Eggerthella*-specific oligonucleotide that specifically hybridizes to a target sequence within a target nucleic acid of an *Eggerthella* species characterized by the presence of a 16S rRNA gene having the nucleobase sequence shown in SEQ ID NO:1, but does not specifically hybridize to a sequence within a nucleic acid from other *Eggerthella* species, (ii) a *Prevotella*-specific oligonucleotide that specifically hybridizes to a target sequence within a target nucleic acid of *P. amnii*, *P. disiens*, and *P. bivia*, but does not specifically hybridize to a sequence within a nucleic acid from other *Prevotella* species, and/or (iii) a *Lactobacillus*-specific oligonucleotide that specifically hybridizes to a target sequence within a target nucleic acid of *Lactobacillus* species, but does not specifically hybridize to a sequence within a nucleic acid from *L. iners*. In typical variations, the reaction mixture includes at least one *Eggerthella*-specific oligonucleotide (e.g., at least two or three *Eggerthella*-specific oligonucleotides, each binding to different target sequences) and at least one *Prevotella*-specific (e.g., at least two or three *Prevotella*-specific oligonucleotides, each binding to different target sequences); in some such variations, the reaction mixture further includes at least one *Lactobacillus*-specific oligonucleotide (e.g., at least two or three *Lactobacillus*-specific oligonucleotides, each binding to different target sequences). The reaction mixture may further include a number of optional components such as, for example, capture probe nucleic acids (e.g., a capture probe for non-specific capture of target nucleic acids) or arrays of capture probe nucleic acids. For an amplification reaction mixture, the reaction mixture will typically include other reagents suitable for performing in vitro amplification such as, e.g., buffers, salt solutions, appropriate nucleotide triphosphates (e.g., dATP, dCTP, dGTP, dTTP, ATP, CTP, GTP and UTP), and/or enzymes (e.g., reverse transcriptase, and/or RNA polymerase), and will typically include test sample components, in which an *Eggerthella*, *Prevotella*, and/or *Lactobacillus* target nucleic acid may or may not be present. For an cleavage-based assay reaction mixture, the reaction mixture will typically include other reagents suitable for performing formation of a cleavage structure, cleavage of the cleavage structure, and detection of the cleavage product, including, e.g., buffers, salt solutions, appropriate nucleotide triphosphates (e.g., dATP, dCTP, dGTP, dTTP, if synthesizing a cDNA from an RNA template), and/or enzymes (e.g., a flap endonuclease and, if synthesizing a cDNA from an RNA template, a reverse transcriptase), and will typically include test sample components, in which an *Eggerthella*, *Prevotella*, and/or *Lactobacillus* target nucleic acid may or may not be present. For a reaction mixture that includes a detection probe together with an amplification oligomer combination, selection of amplification oligomers and detection probe oligomers for a reaction mixture are linked by a common target region (i.e., the reaction mixture will include a probe that binds to a sequence amplifiable by an amplification oligomer combination of the reaction mixture). For a reaction mixture that includes first and second overlapping probe oligonucleotides and a FRET cassette for detection via a cleavage-based assay, oligomers for a reaction mixture are configured such that the FRET cassette will bind to a cleavage product produced by flap endonuclease-mediated cleavage of the cleavage structure formed by the first and second overlapping probe oligonucleotides, where binding of the FRET cassette to the cleavage product forms a secondary substrate for the flap endonuclease.

In some embodiments of a reaction mixture as above, (i) an *Eggerthella*-specific oligonucleotide targets a sequence within an *Eggerthella* 16S rRNA region corresponding to nucleotide positions 615 to 679, (ii) an *Prevotella*-specific oligonucleotide targets a sequence within a *Prevotella* 16S rRNA region corresponding to nucleotide positions 954 to 1037 of SEQ ID NO:2, and/or (iii) a *Lactobacillus*-specific oligonucleotide targets a sequence within a *Lactobacillus* 16S rRNA region corresponding to nucleotide positions 837 to 944 of SEQ ID NO:3. In specific variations of an oligonucleotide targeting an *Eggerthella* 16S rRNA region as above, the *Eggerthella*-specific oligonucleotide includes a target-hybridizing sequence substantially corresponding to, comprising, or consisting of the sequence shown in SEQ ID NO:6; a target-hybridizing sequence substantially corresponding to, comprising, or consisting of the sequence shown in residues 11-27 of SEQ ID NO:4; or a target-hybridizing sequence substantially corresponding to, comprising, or consisting of the sequence shown in residues 1-20 of SEQ ID NO:5. In specific variations of an oligonucleotide targeting a *Prevotella* 16S rRNA region as above, the *Prevotella*-specific oligonucleotide includes a target-hybridizing sequence substantially corresponding to, comprising, or consisting of the sequence shown in SEQ ID NO:9; a target-hybridizing sequence substantially corresponding to, comprising, or consisting of the sequence shown in residues 11-25 of SEQ ID NO:7; or a target-hybridizing sequence substantially corresponding to, comprising, or consisting of the sequence shown in residues 1-24 of SEQ ID NO:8. In specific variations of an oligonucleotide targeting a *Lactobacillus* 16S rRNA region as above, the *Lactobacillus*-specific oligonucleotide includes a target-hybridizing sequence substantially corresponding to, comprising, or consisting of the sequence shown in SEQ ID NO:13; a target-hybridizing sequence substantially corresponding to, comprising, or consisting of the sequence shown in residues 11-27 of SEQ ID NO:10; a target-hybridizing sequence substantially corresponding to, comprising, or consisting of the sequence shown in residues 1-27 of SEQ ID NO:11; or a target-hybridizing sequence substantially corresponding to, comprising, or consisting of the sequence shown in residues 1-32 of SEQ ID NO:12.

The invention is further illustrated by the following non-limiting examples.

Example 1

This example describes a study combining the detection of select *Eggerthella*, *Prevotella*, and *Lactobacillus* species to create a test that was 95.6% sensitive and 97.3% specific (compared to Nugent Score).

Methods

Sample Collection and Participant Demographics

The samples analyzed herein consisted of a subset of the samples collected as part of a larger collection study. A subset of 200 samples, drawn from each of the available collection locations, were chosen for the study described in this example. The 200 samples consisted of 99 samples which were positive for BV according to the criteria used in Cartwright et al. (*Journal of Clinical Microbiology* 51:3694-3699, 2013) and 101 which were negative.

The study population consisted of women attending medical facilities. Women must be 14 years of age or older and sign an IRB-approved waiver. Excluded from the study are premenarchal females and post-menopausal females. The facility collecting the samples was required to also provide Nugent Scores and Amsel criteria results for each sample. Samples used for the analysis herein were collected using vaginal swabs (APTIMA® Vaginal Swab Specimen Collection kit). A total of 80 women were reported to be Caucasian, 111 African American, 2 Native American or Alaska Native, 2 Asian and for 5 subjects no race was recorded.

The sites which collected samples and reported Amsel and Nugent results used in this analysis were University of Alabama at Birmingham (UAB, 50 samples), Louisiana State University (LSU, 50 samples), University of Washington (UOW, 50 samples) and Women's Clinic of Lincoln, Nebr. (WCL, 50 samples).

Real-Time RT-Invader® Chemistry

The ribosomal RNAs of specific bacteria were detected after conversion to cDNA using the Invader® chemistry on a Panther® system. The Invader® reaction relies on the cleavage of a specific nucleic acid structure by the Cleavase® enzyme manufactured by Hologic and has been described elsewhere. See, e.g., Hall et al., *Proc. Natl. Acad. Sci.* 97:8272-8277, 1999; Kaiser et al., *J. Biol. Chem.* 274:21387-21394, 1999. Briefly, the Cleavase® enzyme is derived from a FEN endonuclease which cleaves 5' overhangs. In the Invader detection chemistry there are two reactions which occur. In the primary reaction, a probe is cleaved to release a 5' fragment called the flap and in the secondary reaction, the cleaved flap hybridizes to a FRET molecule creating an overhang which allows cleavage the 5' end of a FRET oligo containing an attached fluorophore. The FRET oligo also contains a quencher which suppresses the release of fluorescence from uncleaved FRETs. When performed on the Panther® instrument for the BV assay, the primary and secondary reactions occur serially at different temperatures. In addition, fluorescence is collected only while the secondary reaction is occurring. The net result is an accumulation of fluorescence which directly relates to the Cleavase® enzyme reaction kinetics. This allows for the estimation of target levels using standard enzyme kinetics or what is commonly known as the initial rate.

The oligos for each assay included a target capture oligo, a single RT primer, an Invader oligo, a probe oligo and a FRET oligo. The target capture oligo in this example was a generic oligo which hybridized to a bead and indiscriminately hybridized to nucleic acid. The RT primer hybridized to the captured target and was extended by a reverse transcriptase, creating a DNA complement of the target. There was no downstream primer so the target region was not amplified. The probe oligo hybridized to the DNA complement of the target region adjacent to the Invader oligo, which creates the 5' overhang in the probe. The flap of the probe was released in an Invader® reaction and the flap hybridized to the FRET, allowing the secondary Invader® reaction to cleave the FRET to release fluorescence.

The Panther instrument processed the samples as follows. The target capture step took place at 64° C. for 28 minutes, which was followed by a 9 minute chill and washing steps (20 minutes). The oligos, enzymes and FRETs are added and the reverse transcription step took place at 44° C. for 11 minutes and 2 seconds. This was followed by the primary reaction step at 64° C. for 20 minutes and 34 seconds, and finally the secondary Invader® reaction took place at 43° C. for about 53 minutes. Since the melting temperature of the flap fragment to the FRET oligo was 43° C., the secondary reaction did not occur until the 43° C. step, which was when fluorescence readings were taken.

Formulations

The oligo mix consisted of 0.5 µM probe oligo, 0.25 µM Invader oligo, 0.2 µM RT-primer, 0.25 µM FRET in buffer (SD PN: TN7294-108). The Enzyme mix consisted of Cleavase X 700 U and MMLV 1500 U, MgCl 18 mM in buffer (SD PN: TN7294-109). All concentrations given were the final reaction concentrations. The target capture reagent consisted of 265 mgs/mL magnetic beads and 0.4 µM capture oligo (wobble probe; 5'-$K_{18}T_3A_{30}$-3'. See e.g., WO 2008/016988 (A9)) in APTIMA® buffer.

Oligo Sequences

The oligo sequences used in this study are included in Table 1.

TABLE 1

Oligo Sequences

| Oligo Type | Target | Sequence (5'→3') | SEQ ID NO |
|---|---|---|---|
| Probe | Eggerthella | GACTAACAACgAGGCAGATGGAATTCC | 4 |
| Invader | Eggerthella | TGGACGACTCGAGTGCGGTAa | 5 |
| RT Primer | Eggerthella | GATATCTGCGCATTCCAC | 6 |
| Probe | Prevotella | GACCCTTATTgGCTAAGCGAAAGCA | 7 |
| Invader | Prevotella | CCGCTGTTAGCACCTAGTGTTAGCa | 8 |
| RT Primer | Prevotella | TTGAGTTTCACCGTTGC | 9 |
| Probe | Lactobacillus | ACAGCAAATAaGGTAGTAACTGGCCTT | 10 |
| Invader | Lactobacillus | AGCTCTGTTGTTGGTGAAGAAGGATAGc | 11 |
| Invader | Lactobacillus | CGTAAAGCTCTGTTGGTAGTGAAGAAAGATAGc | 12 |
| RT Primer | Lactobacillus | TACGTATTACCGCGGCT | 13 |
| FRET* | Eggerthella | (F)TCT(QdT)AGCCGGTTTTCCGGCTGAGAgttgttagtc | 14 |
| FRET | Prevotella | (F)TCT(QdT)AGCCGGTTTTCCGGCTGAGAaataagggtc | 15 |
| FRET | Lactobacillus | (F)TCT(QdT)AGCCGGTTTTCCGGCTGAGAtatttgctgt | 16 |

* For purposes of this study, "F" was FAM in the FRET probe corresponding to SEQ ID NO 14 and was HEX in the FRET probes corresponding to SEQ ID NOs: 15 and 16; "Q" was Blackberry Quencher (BBQ) for all three FRET probes. These labels and label positions are exemplary only, and not limiting.

Oligo Designs Targeting Species Relevant to Bacterial Vaginosis

Figure 5:
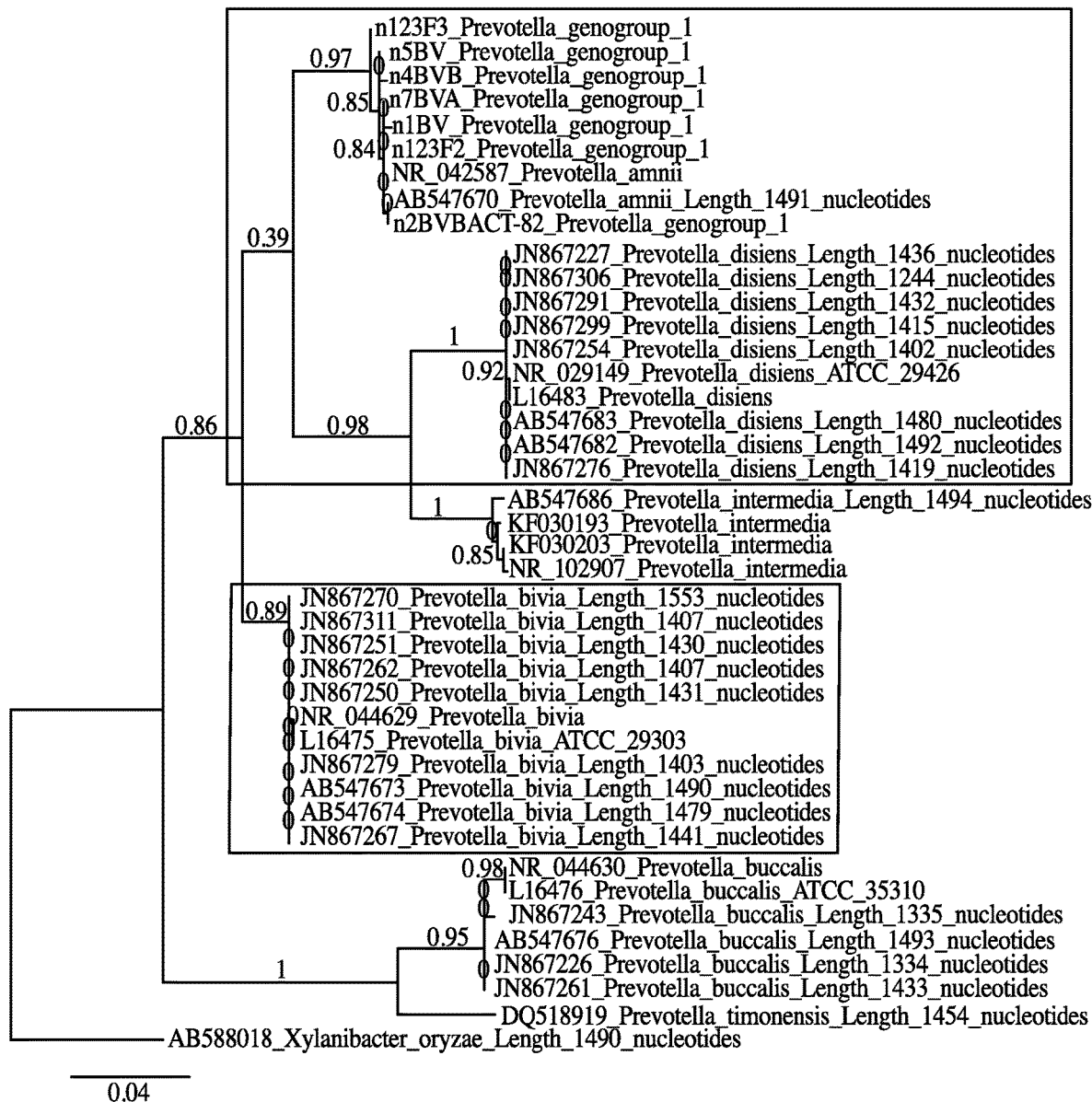
FIG. 5 is a phylogram indicating targeted species of the genus *Prevotella*. Select sequences from the genus *Prevotella* were targeted and are indicated by the boxes. The phylogram was constructed using the maximum likelihood method with a bootstrap value of 100. The number at each branch choice indicates the frequency of the branch choice.
Figure 6:
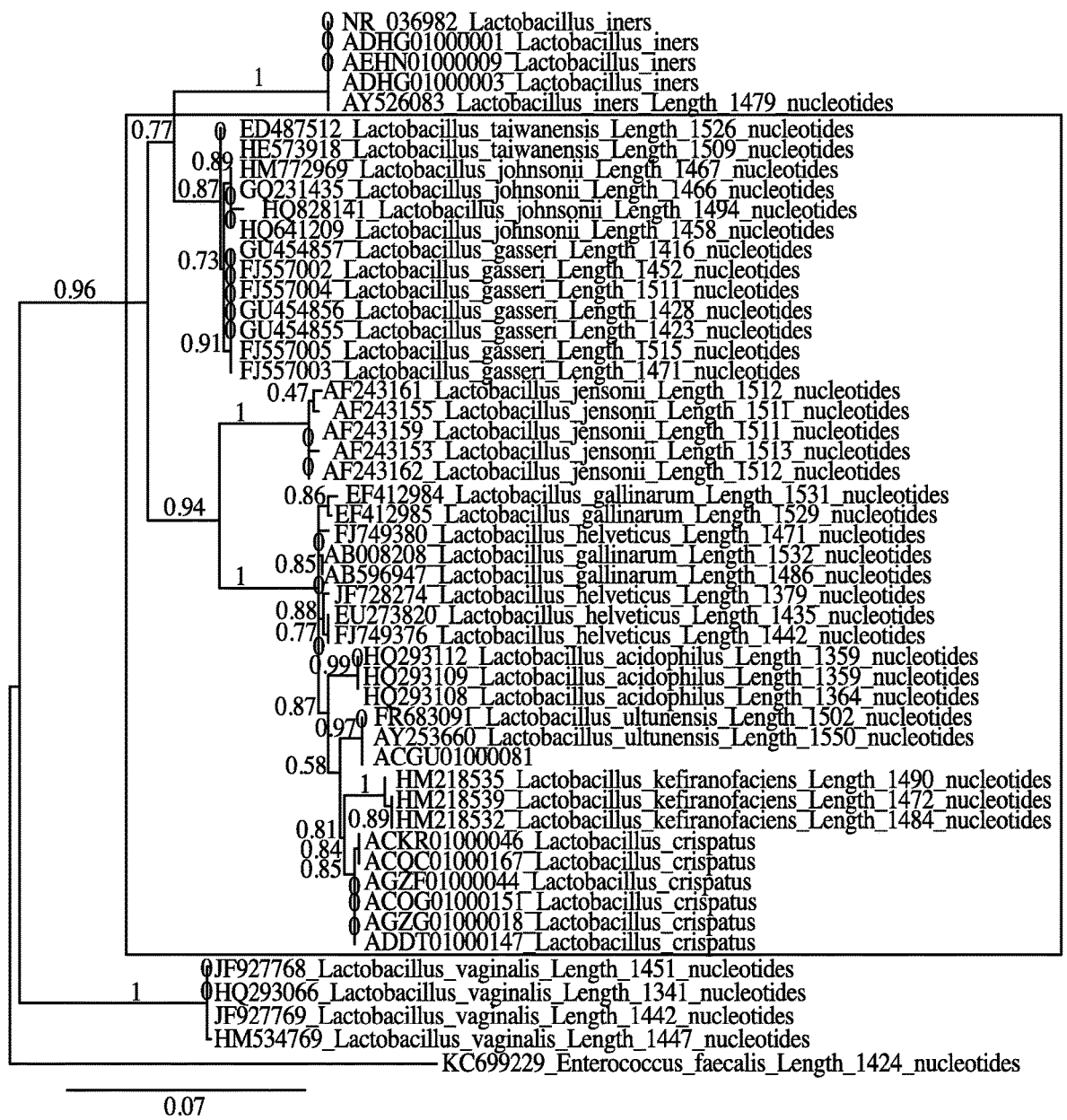
FIG. 6 is a phylogram indicating targeted species of the genus *Lactobacillus*. Select sequences from the genus *Lactobacillus* were targeted and are indicated by the box. The phylogram was constructed using the maximum likelihood method with a bootstrap value of 100. The number at each branch point indicates the frequency of the branch choice.

Oligos were designed to target only the most relevant species within each genus for the determination of bacterial vaginosis. The oligos which target species in the genus *Lactobacillus*, did not detect the *L. iners* species. The oligos which targeted *Eggerthella* and *Prevotella* were similarly designed to target only select members of these genera. The phylograms in FIGS. 4, 5, and 6 indicate the targeted species within each genus and the relationship to closely related species.

In the case of *Eggerthella*, the focus of the design was an uncultured species found in the vaginal environment. See Fredricks et al., *J. Clin. Microbiol.* 45:3270-3276, 2007. For the *Prevotella* design, species which tended to complement the BV association of the *Eggerthella* design were chosen. Specifically, *P. amnii*, *P. disiens* and *P. bivia* were targeted and other closely related species of *Prevotella* were not. This approach is believed to have improved sensitivity without sacrificing specificity as might be expected if all *Prevotella* species were included.

Fluorescence Data Collection and Analysis

The Panther instrument collected fluorescence readings for four colors at roughly 24 second intervals during the 43° C. step in the process. The signal generated was corrected for the effects of bleed-through, detector gain and detector offset using previously obtained calibrated values obtained using controlled amounts of fluorescence dye and blanks. Alternative corrections were explored which did not require dye calibration and were found to be equally effective. The initial rate of the reaction was then calculated from the initial linear portion of the curve. For convenience, this rate was multiplied by 1,000,000. This value is called Velocity (V).

Velocity Thresholds and Determining BV Status from Assays

Figure 8:
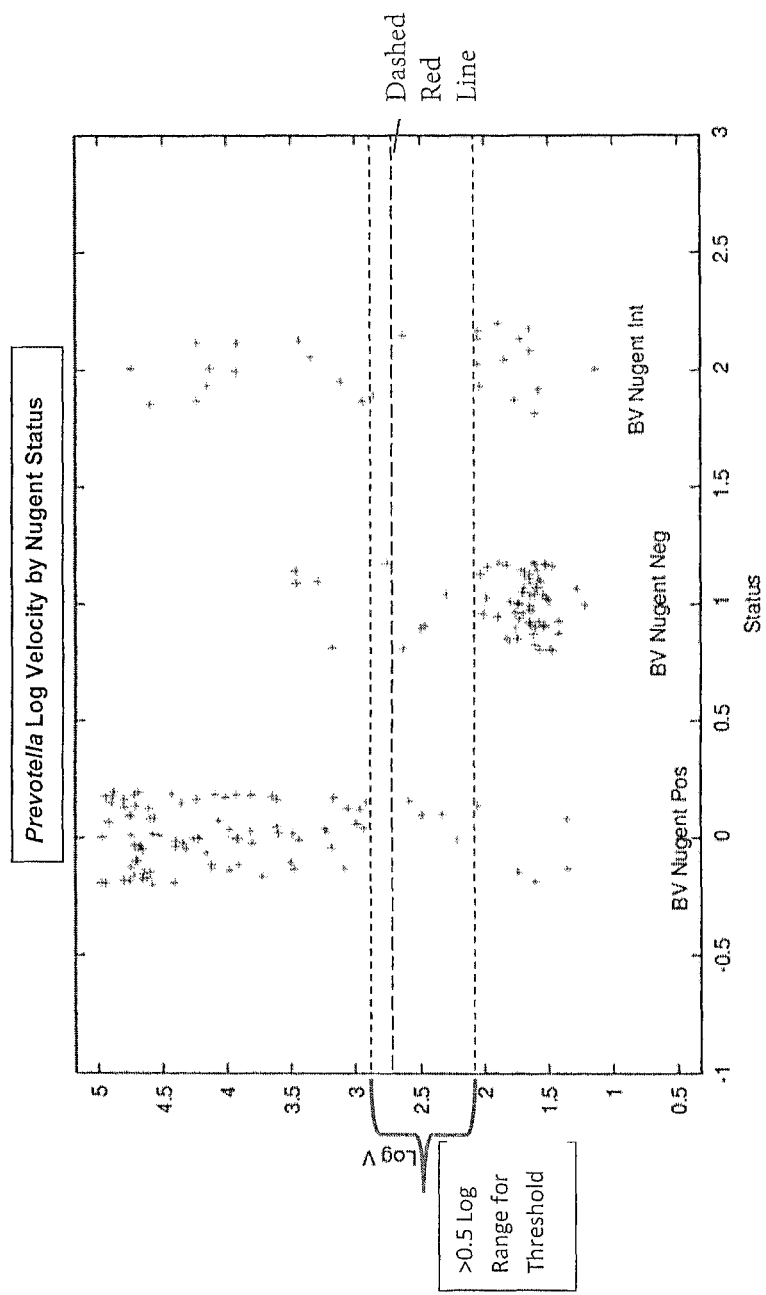
FIG. 8 depicts log Velocity and BV status for select species of *Prevotella* showing the separation between Nugent positive and Nugent negative samples (see Example 1). The threshold value used in the Example 1 study is indicated by the dashed red line.
Figure 9:
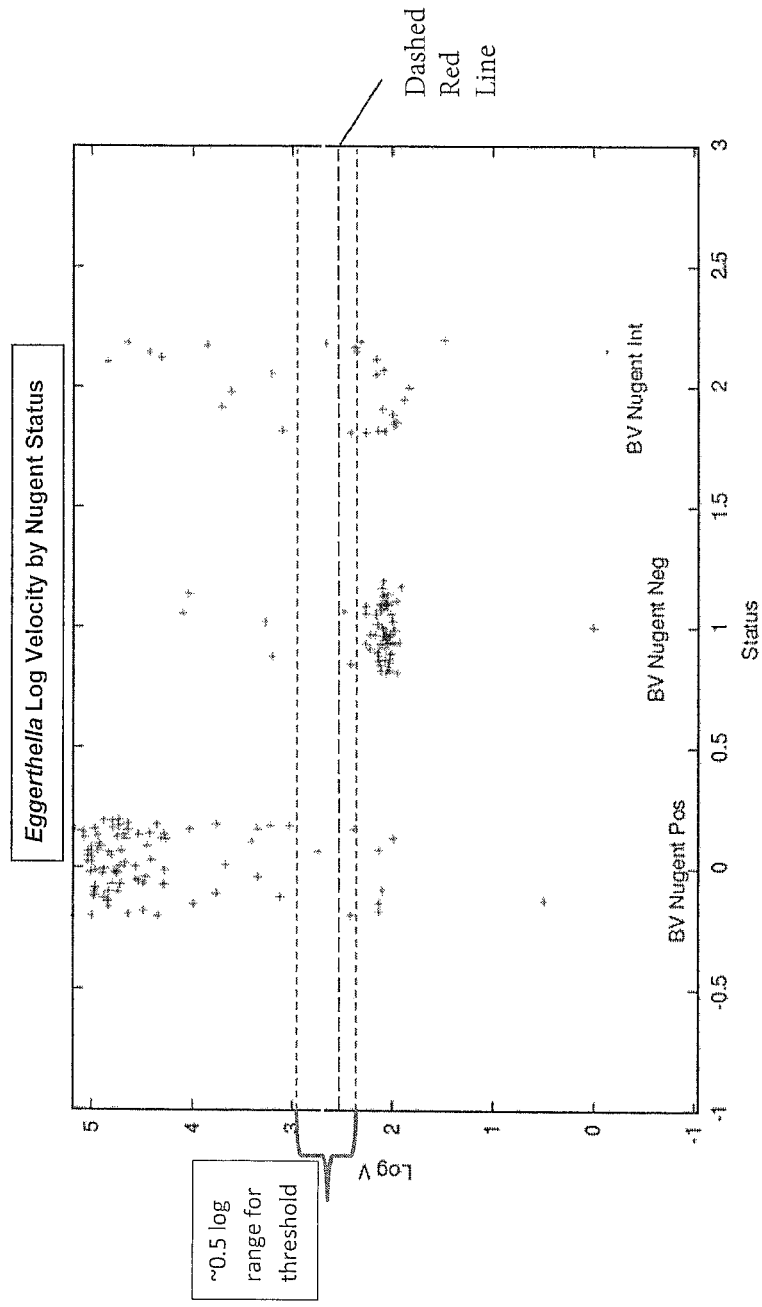
FIG. 9 depicts log Velocity and BV status for select species of *Eggerthella* showing the separation between Nugent positive and Nugent negative samples (see Example 1). The threshold value used in the Example 1 study is indicated by the dashed red line.
Figure 10:
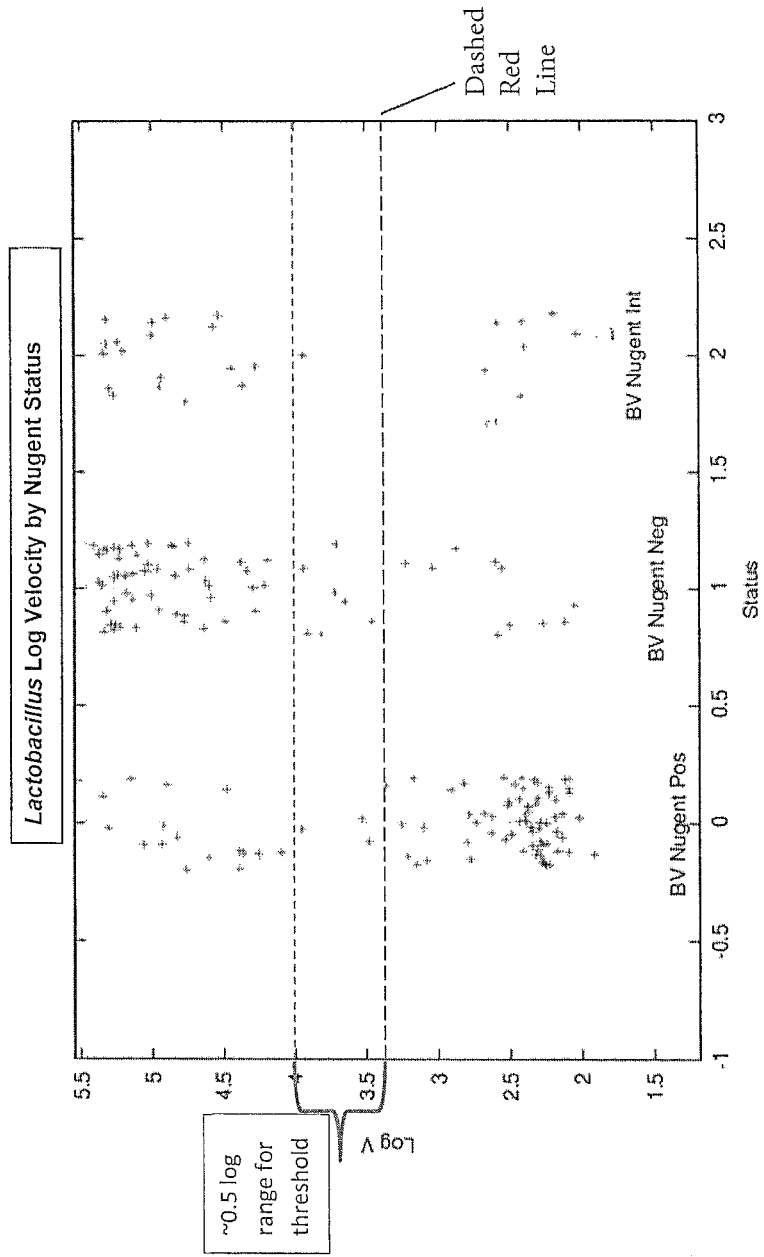
FIG. 10 depicts log Velocity and BV status for select species of *Lactobacillus* showing the separation between Nugent positive and Nugent negative samples (see Example 1). The threshold value used in the Example 1 study is indicated by the dashed red line.

Thresholds for each target were determined using the entire study population. For each of the three targets, a range of roughly 0.5 logs in Velocity was the observed separation between most Nugent positive and Nugent negative samples. For this study, the following threshold values were used. For *Prevotella*, the threshold was set to a log V value of 2.67 (see FIG. 8); for *Eggerthella*, the threshold was set to a log V value of 2.58 (see FIG. 9); and for *Lactobacillus*, the threshold was set to a log V value of 3.44 (see FIG. 10).

Figure 7:
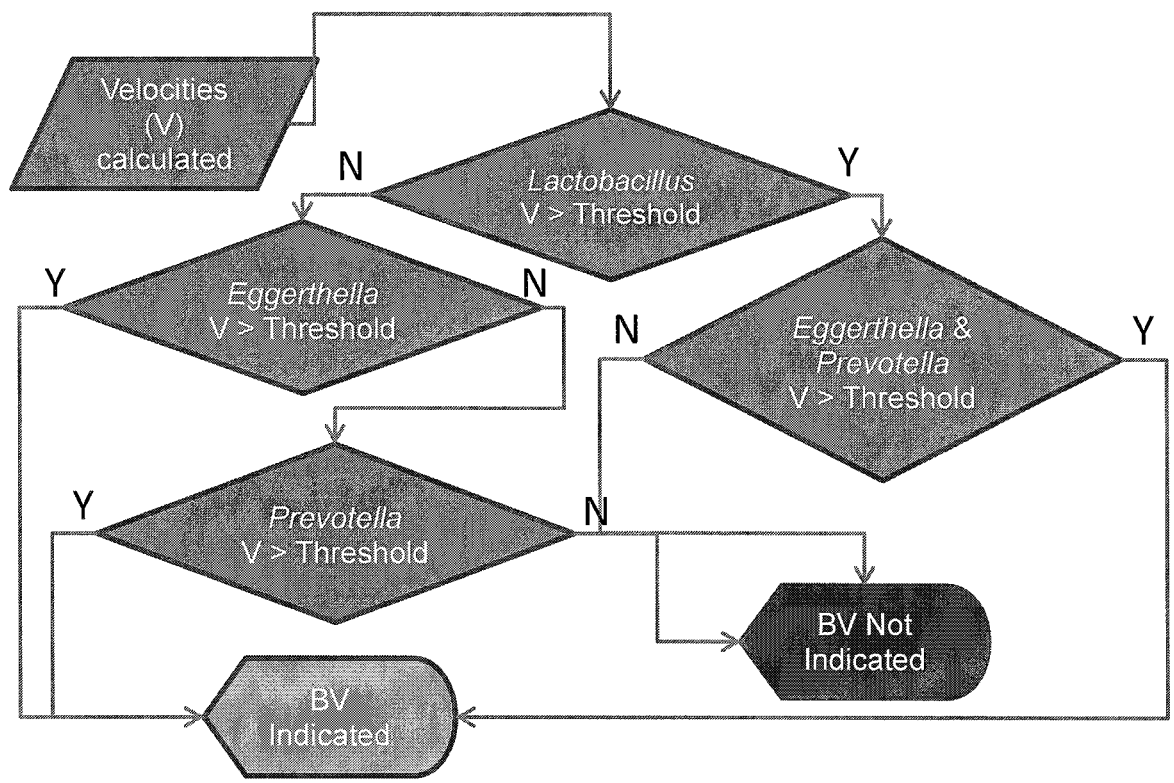
FIG. 7 is a flow diagram depicting the logic used to make bacterial vaginosis status indications from assay Velocities (V) (see Example 1). When the selected *Lactobacillus* Velocity is equal to or below threshold, V values for either *Eggerthella* or *Prevotella* above threshold result in a positive indication for bacterial vaginosis. When the *Lactobacillus* V value is above the threshold, the V values for both *Eggerthella* and *Prevotella* must be above the threshold for BV to be indicated.

For each sample with a velocity value above the threshold, a value of 1 was assigned; otherwise, a value of zero was assigned. This value determination was performed for each target. For *Eggerthella* alone, this result was compared to either the composite result or Nugent Score. For the combination of select *Eggerthella*, *Prevotella*, and *Lactobacillus* species, the individual target results were combined as represented in the flow chart shown in FIG. 7. Simply, when the velocity (V) for *Lactobacillus* was equal to or below the threshold, samples with V values above threshold for either *Eggerthella* or *Prevotella* were considered positive (indicative of BV). When the velocity (V) for *Lactobacillus* was above the threshold, samples with V values above threshold for both *Eggerthella* and *Prevotella* were considered positive. All other samples were considered to be BV negative (not indicative of BV). This determination logic can also be represented as follows: BV Score=b1+b2−g1, where b1 and b2 represent *Eggerthella* and *Prevotella*, respectively, g1 represents *Lactobacillus*, values assigned to b1, b2 and g1 are 0 or 1 depending on whether the V value is equal-or-below or above the threshold, respectively; a BV score of 1 or greater is BV positive.

Using the above logic, the assays were used to determine BV status and this status was correlated with a composite comparator or Nugent Score for 200 samples.

Results

The two accepted methods of determining BV status in women are the Nugent Score and Amsel Criteria. Each is often used on its own to determine whether or not a woman should be treated for bacterial vaginosis, suggesting these are two different methods which detect the same condition. A comparison of Amsel Criteria results to Nugent Score determinations showed relatively poor performance of each test against the other. See Table 2. These results were similar to previous observations. See Schwebke et al., *Obstetrics & Gynecology* 88:573-576, 1996; Mastrobattista et al., *Obstetrics & Gynecology* 96:504-506, 2000. For laboratory purposes, the Nugent Score is considered to be the gold standard. Unfortunately, a significant percentage of women will have Nugent Scores which fall into the intermediate range making diagnosis difficult. In the study group of this example, 16% of all subjects had Nugent Scores in the intermediate range.

TABLE 2

Amsel Criteria and Nugent Score Compared

|  | Nugent | | | |
| --- | --- | --- | --- | --- |
|  | Pos | Neg | Intermediate | Total |
| Amsel Pos | 61 | 6 | 8 | 75 |
| Amsel Neg | 30 | 67 | 28 | 125 |
| Total | 91 | 73 | 36 | 200 |

When measured against the Nugent Score as the gold standard, the Amsel Criteria were found to be 67.0% sensitive and 91.8% specific. In this case, 36 Nugent intermediate samples were excluded from the analysis because these are neither true positive nor true negative. When measured against the Amsel Criteria, the Nugent Score was found to be 81.3% sensitive and 76.0% specific when Nugent Score intermediates were considered to be negative. When the Nugent Score intermediates were considered to be positive, the Nugent Score was 92.0% sensitive and 53.6% specific when measured against the Amsel Criteria. Excluding 36 Nugent Score intermediate samples yielded 91.0% sensitivity and 69.1% specificity for the Nugent Score when compared to the Amsel Criteria.

The performance of the Real-time RT-Invader assay for *Eggerthella* was compared to a composite comparator which combines Amsel Criteria and Nugent Score. See Table 3. For the composite comparator, a sample was positive only if the Amsel Criteria results and the Nugent Score results were positive and a sample was negative only if the Amsel Criteria results and the Nugent Score results were negative. All other samples were excluded, resulting in a total of 129 samples in this analysis. The performance of the assay was also compared to Nugent Score alone. See Table 4.

TABLE 3

Real-time RT-Invader assay for *Eggerthella* compared to Amsel/Nugent Composite Comparator

|  | Pos | Neg | Total |
| --- | --- | --- | --- |
| *Eggerthella* Positive | 61 | 5 | 66 |
| *Eggerthella* Negative | 0 | 63 | 63 |
| Total | 61 | 68 | 129 |

TABLE 4

Real-time RT-Invader assay for *Eggerthella* compared to Nugent Score

|  | Nugent Score | | | |
|---|---|---|---|---|
|  | Pos | Neg | Intermediate | Total |
| *Eggerthella* Positive | 84 | 4 | 13 | 101 |
| *Eggerthella* Negative | 7 | 69 | 23 | 99 |
| Total | 91 | 73 | 36 | 200 |

When the Real-time RT-Invader assay for *Eggerthella* alone was compared to a composite comparator, 100.0% sensitivity and 92.6% specificity were found. When the Real-time RT-Invader assay for *Eggerthella* was compared to the Nugent Score, a sensitivity of 92.3% and a specificity of 94.5% were found (with 36 Nugent Score intermediate samples excluded).

In addition to *Eggerthella*, the performance of assays which combine the detection of several bacteria species were examined. Tables 5 and 6 summarize the performance of an assay which targeted select *Eggerthella*, *Prevotella*, and *Lactobacillus* species.

TABLE 5

Real-time RT-Invader assay for *Eggerthella*, *Prevotella* & *Lactobacillus* compared to Amsel/Nugent Composite Comparator

|  | Composite Comparator | | |
|---|---|---|---|
|  | Pos | Neg | Total |
| Assay Positive | 61 | 3 | 64 |
| Assay Negative | 0 | 65 | 65 |
| Total | 61 | 68 | 129 |

TABLE 6

Real-time RT-Invader assay for *Eggerthella*, *Prevotella* & *Lactobacillus* compared to Nugent Score

|  | Nugent Score | | | |
|---|---|---|---|---|
|  | Pos | Neg | Intermediate | Total |
| Assay Positive | 87 | 2 | 15 | 104 |
| Assay Negative | 4 | 71 | 21 | 96 |
| Total | 91 | 73 | 36 | 200 |

When compared to the composite comparator (Table 5), the assay performed with 100% sensitivity and 95.6% specificity. The assay combination of select *Eggerthella*, *Prevotella* and *Lactobacillus* species produced a test which is 95.6% sensitive and 97.3% specific when compared to Nugent Score (36 Nugent Score intermediate samples excluded).

Discussion

Figure 11:
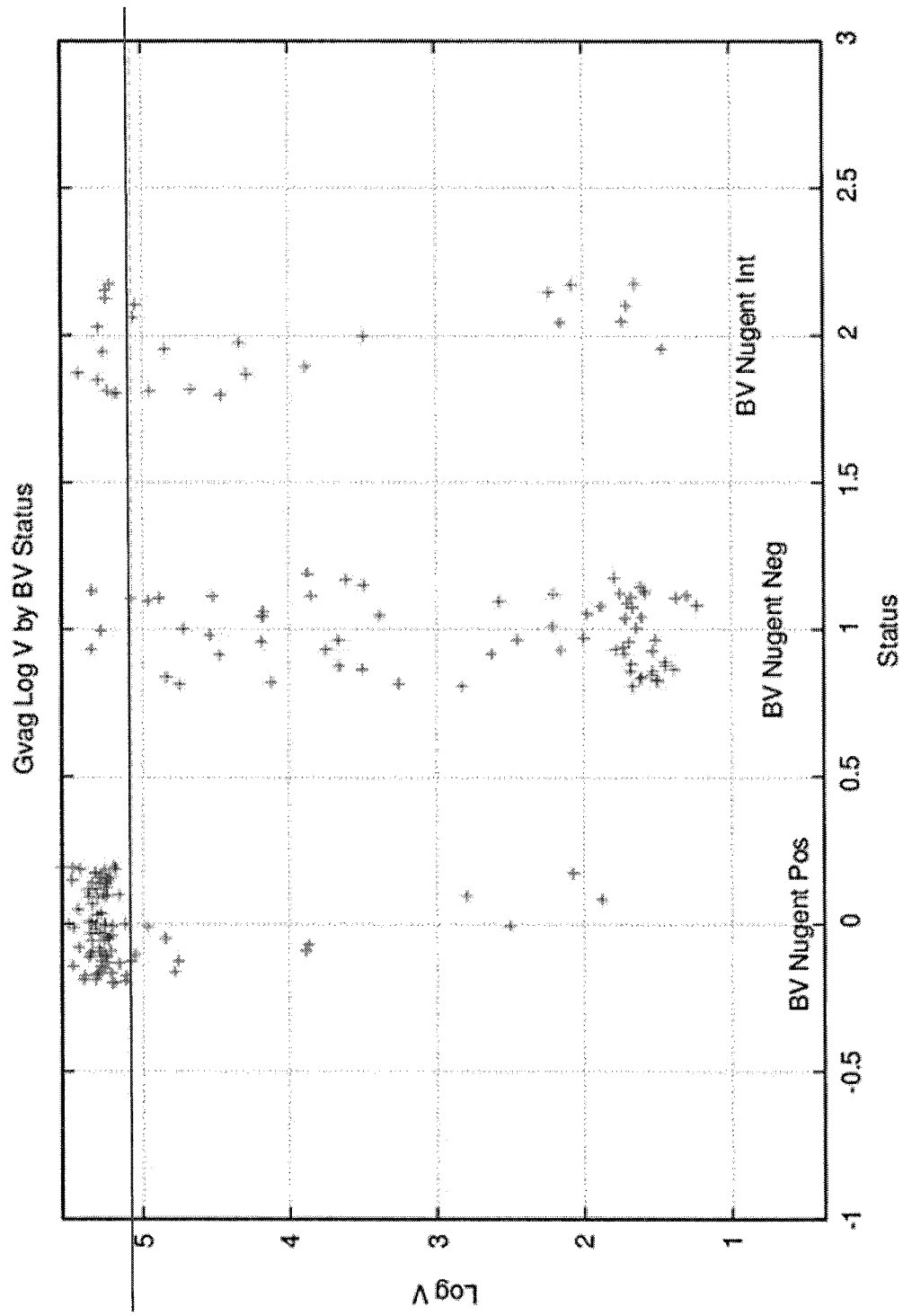
FIG. 11 depicts log Velocity and BV status for select species of *G. vaginalis* showing the separation between Nugent positive and Nugent negative samples.
Figure 12:
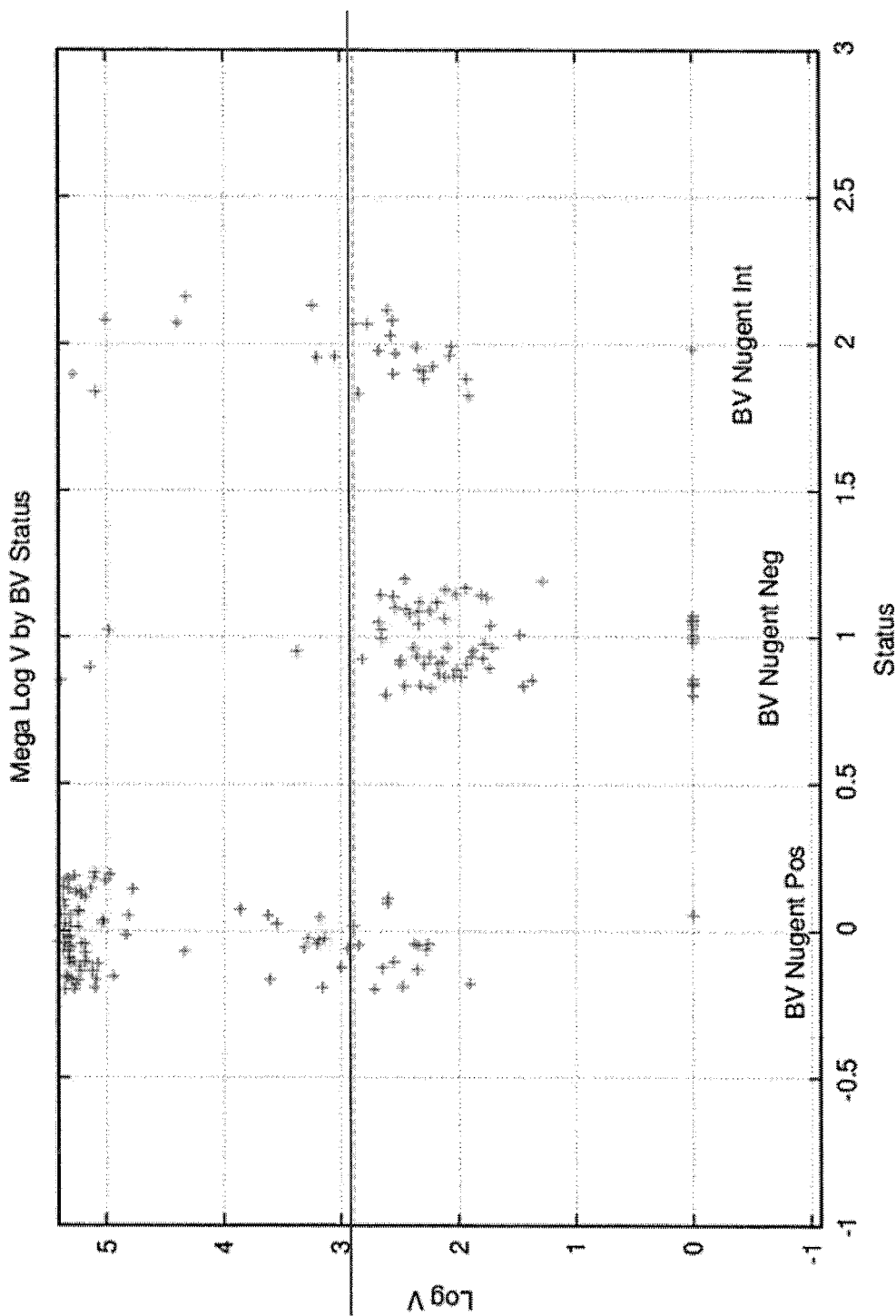
FIG. 12 depicts log Velocity and BV status for select species of *Megasphaera* type 1 showing the separation between Nugent positive and Nugent negative samples.

The results for *Eggerthella* indicate that a test utilizing *Eggerthella* alone would significantly out-perform the only FDA-approved test on the market today when compared to the Nugent Score. Further, among the bacteria usually targeted for the diagnosis of BV, the *Eggerthella* assay was found to be specific and reasonably sensitive while maintaining a very clear separation between the Nugent positive and negative samples (see FIG. 9). For contrast, high-abundance targets such as *Gardnerella vaginalis* tended to display a continuum of assay readings (log V) between Nugent positive and negative samples (see FIG. 11). For a targets such as *Megasphaera* type 1 (see FIG. 12), high specificity is possible but at a considerable cost to sensitivity.

Previous studies have focused on combining bacterial indicators of dysbiosis for the purpose of diagnosing bacterial vaginosis. In the study of this example, targets were selected and assays designed such that the *Eggerthella* and *Prevotella* assay have largely over-lapping and complementary sensitivities. In 8 out of 91 Nugent positive samples (9%), either the *Eggerthella* assay was positive or the *Prevotella* assay was positive but not both. In 80 out of 91 Nugent positive samples (88%), both the *Eggethella* and *Prevotella* assays were positive.

In Ravel et al. (*J. Clin. Micobiol.* 51:3694-3699, 2011), *Prevotella* was found 65% of the time in a population of asymptomatic women, suggesting that targeting this genus would result in false positive results. When designing the *Prevotella* assay of this example, only a few specific species of that genus were targeted. In addition, the combination of results for *Eggerthella* and *Prevotella*, as highly specific indicators for BV, was tied with the *Lactobacillus* results as an indicator of vaginal health. This approach uniquely raised both the sensitivity and specificity of the combined assay. Both sensitivity and specificity were improved by combining the *Eggerthella* assay with assays for select *Prevotella* species and select *Lactobacillus* species.

Figure 13:
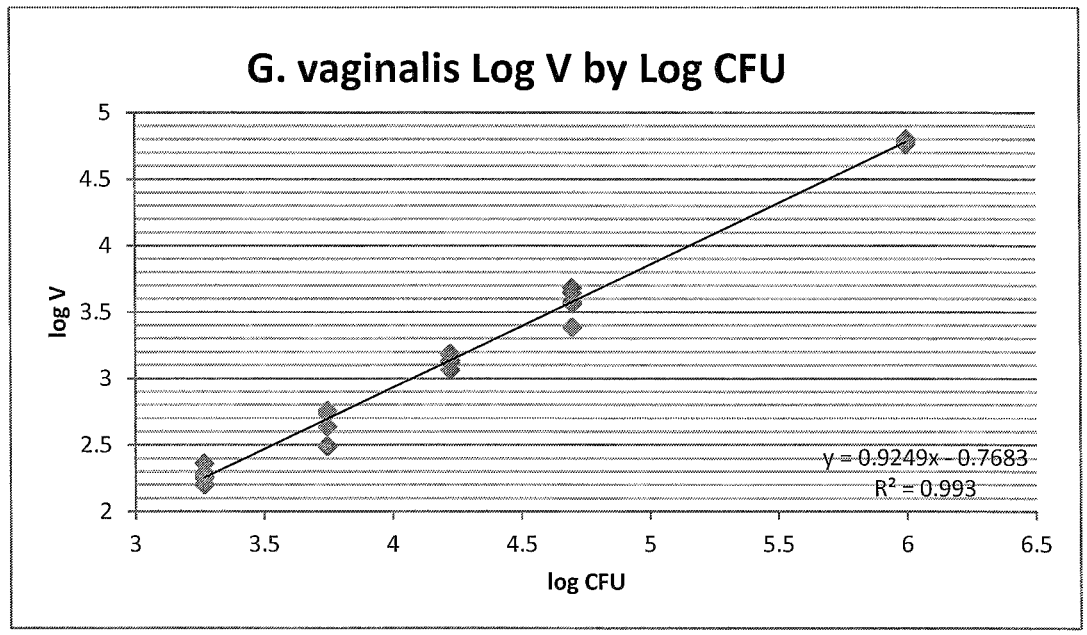
FIG. 13 depicts the relationship of log Velocity to log concentration of a bacterial target.

An underlying assumption of the assays is that Velocity relates to the abundance of the bacterial target in the sample. This was established in previous experiments using a titration of controlled amount of bacterial target (example provided in FIG. 13).

The studies of this example demonstrated, inter alia, the clinical utility of targeting select *Eggerthella* species for the diagnosis of BV. In this study, performance (92.3% sensitivity/93.5% specificity) which exceeded that of the only FDA-approved test for BV on the market today. Further, unlike assays directed to some other targets, the *Eggerthella* assay gave a result which clearly distinguishes between Nugent positive and Nugent negative samples. Combining the result of the *Eggerthella* assay with *Prevotella* and *Lactobacillus* resulted in a test for BV that is highly sensitive (95.6%) and specific (97.3%) when compared to the Nugent Score. Uniquely, the results of these three assays were combined using a logic which changes dependent on the result of the *Lactobacillus* assay to obtain greater sensitivity and specificity.

From the foregoing, it will be appreciated that, although specific embodiments of the invention have been described herein for purposes of illustration, various modifications may be made without deviating from the spirit and scope of the invention. Accordingly, the invention is not limited except as by the appended claims. All publications, patents, and patent applications cited herein are hereby incorporated by reference in their entireties for all purposes.

What is claimed is:

1. A reaction mixture for specific detection of an *Eggerthella* target nucleic acid and a *Prevotella* target nucleic acid in the presence of other nucleic acids that may be in a sample, the reaction mixture comprising:

an *Eggerthella*-specific oligonucleotide that specifically hybridizes to a target sequence within a target nucleic acid of an *Eggerthella* species characterized by the presence of a 16S rRNA gene having a nucleobase sequence that is at least 98% identical to the sequence shown in SEQ ID NO:1, but does not specifically hybridize to a sequence within a nucleic acid from other *Eggerthella* species, wherein the *Eggerthella*-specific oligonucleotide comprises a 3' portion that specifically hybridizes to the target sequence within the *Eggerthella* target nucleic acid and a 5' portion that does not specifically hybridize to the *Eggerthella* target nucleic acid, wherein the 3' portion of the *Eggerthella*-specific oligonucleotide is a target-hybridizing sequence consisting of the sequence shown in residues 11-27 of SEQ ID NO:4, and a *Prevotella*-specific oligonucleotide that specifically hybridizes to a target sequence within a target nucleic acid of *P. amnii*, *P. disiens*, and *P. bivia*, but does not specifically hybridize to a sequence within a nucleic acid from other *Prevotella* species, wherein the *Prevotella*-specific oligonucleotide comprises a 3' portion that specifically hybridizes to the target sequence within the *Prevotella* target nucleic acid and a 5' portion that does not specifically hybridize to the *Prevotella* target nucleic acid, wherein the 3' portion of the *Prevotella*-specific oligonucleotide is a target-hybridizing sequence consisting of the sequence shown in residues 11-25 of SEQ ID NO:7, optionally wherein the reaction mixture further comprises a *Lactobacillus*-specific oligonucleotide that specifically hybridizes to a target sequence within a target nucleic acid of *Lactobacillus* species, but does not specifically hybridize to a sequence within a nucleic acid from *L. iners*, wherein the *Lactobacillus*-specific oligonucleotide comprises a 3' portion that specifically hybridizes to the target sequence within the *Lactobacillus* target nucleic acid and a 5' portion that does not specifically hybridize to the *Lactobacillus* target nucleic acid.

2. The reaction mixture of claim 1, wherein the *Eggerthella* and *Prevotella* target nucleic acids are 16S rRNAs of *Eggerthella* and *Prevotella*, respectively, and wherein if the reaction mixture further comprises the *Lactobacillus*-specific oligonucleotide, then the *Lactobacillus* target nucleic acid is a 16S rRNA of *Lactobacillus*.

3. The reaction mixture of claim 2, wherein
the 3' portion of the *Lactobacillus*-specific oligonucleotide, if present, is a target-hybridizing sequence consisting of the sequence shown in residues 11-27 of SEQ ID NO:10.

4. The reaction mixture of claim 3, wherein the reaction mixture comprises the *Lactobacillus*-specific oligonucleotide, and wherein the reaction mixture further comprises
(i) second and third *Eggerthella*-specific oligonucleotides that target a sequence within an *Eggerthella* 16S rRNA region corresponding to nucleotide positions 615 to 679 of SEQ ID NO: 1; and/or
(ii) second and third *Prevotella*-specific oligonucleotides that target a sequence within a *Prevotella* 16S rRNA region corresponding to nucleotide positions 954 to 1037 of SEQ ID NO:2; and/or
(iii) second and third *Lactobacillus*-specific oligonucleotides that target a sequence within a *Lactobacillus* 16S rRNA region corresponding to nucleotide positions 837 to 944 of SEQ ID NO:3.

5. The reaction mixture of claim 3, wherein the reaction mixture comprises the *Lactobacillus*-specific oligonucleotide.

6. The reaction mixture of claim 4, wherein the second *Eggerthella*-specific oligonucleotide comprises a target-hybridizing sequence corresponding to the sequence shown in residues 1-20 of SEQ ID NO:5, and wherein the third *Eggerthella*-specific oligonucleotide comprises a target-hybridizing sequence corresponding to the sequence shown in SEQ ID NO:6.

7. The reaction mixture of claim 4, wherein the second *Prevotella*-specific oligonucleotide comprises a target-hybridizing sequence corresponding to the sequence shown in residues 1-24 of SEQ ID NO:8, and wherein the third *Prevotella*-specific oligonucleotide comprises a target-hybridizing sequence corresponding to the sequence shown in SEQ D NO:9.

8. The reaction mixture of claim 4, wherein the second *Lactobacillus*-specific oligonucleotide is selected from the group consisting of (i) an oligonucleotide comprising a target-hybridizing sequence corresponding to the sequence shown in residues 1-27 of SEQ ID NO: 11 and (ii) an oligonucleotide comprising a target-hybridizing sequence corresponding to the sequence shown in residues 1-32 of SEQ ID NO: 12, and wherein the third *Lactobacillus*-specific oligonucleotide comprises a target-hybridizing sequence corresponding to the sequence shown in SEQ ID NO: 13.

9. The reaction mixture of claim 1, wherein the reaction mixture comprises the *Lactobacillus*-specific oligonucleotide.

* * * * *